(12) United States Patent
Takahashi et al.

(10) Patent No.: US 10,615,677 B2
(45) Date of Patent: Apr. 7, 2020

(54) ACTUATOR, AIR PUMP, BEAUTY TREATMENT DEVICE, AND LASER SCANNING DEVICE

(71) Applicants: Yuki Takahashi, Tokyo (JP); Shigenori Inamoto, Tokyo (JP)

(72) Inventors: Yuki Takahashi, Tokyo (JP); Shigenori Inamoto, Tokyo (JP)

(73) Assignee: MITSUMI ELECTRIC CO., LTD., Tokyo (JP)

( * ) Notice: Subject to any disclaimer, the term of this patent is extended or adjusted under 35 U.S.C. 154(b) by 247 days.

(21) Appl. No.: 15/305,907

(22) PCT Filed: Apr. 23, 2015

(86) PCT No.: PCT/JP2015/002214
§ 371 (c)(1),
(2) Date: Oct. 21, 2016

(87) PCT Pub. No.: WO2015/162933
PCT Pub. Date: Oct. 29, 2015

(65) Prior Publication Data
US 2017/0047835 A1 Feb. 16, 2017

(30) Foreign Application Priority Data

Apr. 25, 2014 (JP) ................................ 2014-091860

(51) Int. Cl.
*H02K 33/12* (2006.01)
*H02K 33/00* (2006.01)
(Continued)

(52) U.S. Cl.
CPC ............ *H02K 33/00* (2013.01); *A61B 5/022* (2013.01); *F04B 45/047* (2013.01); *G01S 7/481* (2013.01); *H02K 33/12* (2013.01)

(58) Field of Classification Search
CPC .................. H02K 1/2713; H02K 33/00–33/18
See application file for complete search history.

(56) References Cited

U.S. PATENT DOCUMENTS 4,602,848 A   7/1986  Honds et al.
4,764,695 A   8/1988  Inoue et al.
(Continued)

FOREIGN PATENT DOCUMENTS

EP   0103929 A2   3/1984
EP   0206396 A1   12/1986
(Continued)

OTHER PUBLICATIONS

Extended European Search Report for EP Patent Application No. 15782350.1, dated Nov. 22, 2017.
(Continued)

*Primary Examiner* — Ramon M Barrera
(74) *Attorney, Agent, or Firm* — Brundidge & Stanger, P.C.

(57) ABSTRACT

An actuator includes: a movable body including a single-pole magnetized single pole magnet; and a plurality of electromagnets each having a magnetic core portion and a coil portion for exciting the core portion. The actuator has: a fixed body on which three or more magnetic poles of the electromagnets are disposed at positions orthogonal to the magnetization direction of the single-pole magnet; and an elastic body bridged between the movable body and the fixed body and elastically deforming when current is supplied to the coil portion, thereby supporting the movable body so as to be movable in the magnetization direction of the single-pole magnet and the two-degree-of-freedom direction. The elastic body is attached to the movable body so that the movable center of the movable body matches the substantial center of the generated magnetic torque of the movable body.

15 Claims, 12 Drawing Sheets

(51) Int. Cl.
　　　　*A61B 5/022*　　　(2006.01)
　　　　*F04B 45/047*　　(2006.01)
　　　　*G01S 7/481*　　　(2006.01)

(56) References Cited

U.S. PATENT DOCUMENTS

| | | |
|---|---|---|
| 5,252,870 A | 10/1993 | Jacobsen et al. |
| 5,596,442 A | 1/1997 | Plesko |
| 6,188,502 B1 | 2/2001 | Aoki |
| 2001/0000130 A1 | 4/2001 | Aoki |
| 2008/0169891 A1 | 7/2008 | Umeda et al. |

FOREIGN PATENT DOCUMENTS

| | | |
|---|---|---|
| GB | 624530 A | 6/1949 |
| JP | 8-65990 A | 3/1996 |
| JP | 3038707 B1 | 5/2000 |
| JP | 2003-116255 A | 4/2003 |
| JP | 2010-57226 A | 3/2010 |
| JP | 2011-000556 A | 1/2011 |
| JP | 4617554 B2 | 1/2011 |
| JP | 2011-128203 A | 6/2011 |
| JP | 4757573 B2 | 8/2011 |
| JP | 2012-191817 A | 10/2012 |

OTHER PUBLICATIONS

Office Action for EP Patent Application No. 15782350.1, dated Aug. 7, 2018.
International Search Report from International Application No. PCT/JP2015/002214 dated Jul. 14, 2015.
Office Action for EP Patent Application No. 15782350.1, dated May 20, 2019.

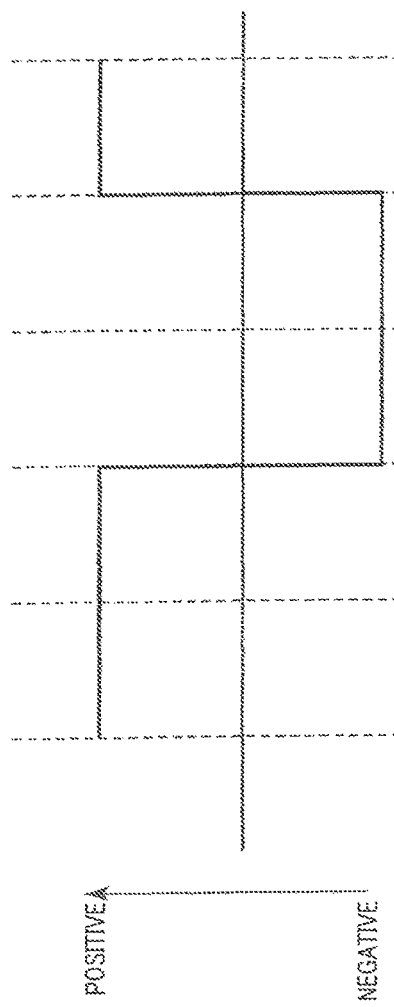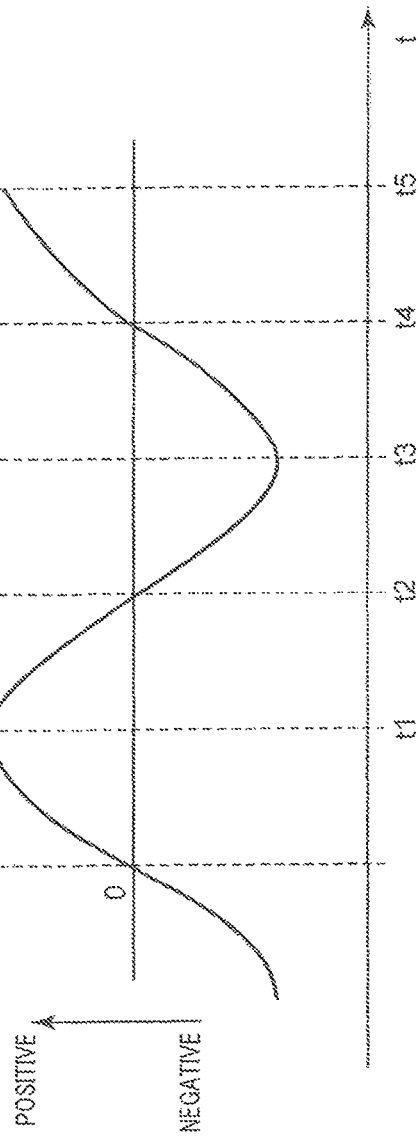
FIG. 6A
FIG. 6B

ACTUATOR, AIR PUMP, BEAUTY TREATMENT DEVICE, AND LASER SCANNING DEVICE

TECHNICAL FIELD

The present invention relates to an actuator that can perform precession around a predetermined rotation axis at a predetermined angle, and an air pump, an aesthetic apparatus and a laser scanning apparatus which include the actuator.

BACKGROUND ART

Conventionally, the small-sized pump disclosed in PTL 1 has been known as an air pump used for a sphygmomanometer and the like, for example.

The small-sized pump is provided with a plurality of diaphragms for forming a pump chamber in the case. A cylindrical exhaust valve is formed at a center portion of the pump chamber. In addition, the pump chamber is provided with a suction valve. The diaphragms are connected with a swing member, and are vertically moved when the swing member swings with an eccentric rotation shaft. The eccentric rotation shaft is fixed with eccentricity to a disk part fixed to the rotation shaft of a DC motor disposed below the eccentric rotation shaft.

In the small-sized pump, when the DC motor is driven into rotation, the eccentric rotation shaft rotates with eccentricity to swing the swing member and vertically move the diaphragms in an alternate manner, thus performing suction from the suction valve and exhaustion from the exhaust valve. That is, in the small-sized pump, the rotation of the DC motor that performs typical axial rotation is converted into precession with use of the eccentric rotation shaft and the swing member in order to vertically move the diaphragms.

Known examples of the driving part for precession include the biaxial type actuator disclosed in PTL 2 and the swing driving apparatus disclosed in PTL 3.

The actuator of PTL 2 is used for a holography apparatus, which adjusts the incident angle of reference light with respect to the optical recording medium by setting the reflection mirror at a desired inclination angle. To be more specific, the actuator includes a movable shaft for supporting the control object, and a support mechanism for swingably supporting the movable shaft with respect to a third axis (Z axis) as a reference shaft that is perpendicular to a first virtual axis and a second virtual axis orthogonal to each other. With use of a magnetic circuit composed of a magnet and a coil, the movable shaft is tilted relative to the orientation that coincides with the reference shaft.

In addition, PTL 3 discloses a swing driving apparatus for swinging an antenna used in the space. PTL 3 discloses an elastic support mechanism disposed between an antenna and a seat for supporting the antenna on the back side. The elastic support mechanism supports the antenna at a center point on the back side, and swingably mounts the antenna around two axes orthogonal to each other. The elastic support mechanism is formed of an elastic material, and includes an elastic shaft whose one end is fixed at a center of the back of the antenna and the other end is fixed to a center of the seat, and leaf springs that are disposed at approximately 90 degrees with respect to each other and whose one end is fixed to at a center of the back of the antenna and other end is fixed at four points on the seat. The antenna swings by the actuator that exerts a force on the antenna supported by the elastic support mechanism.

CITATION LIST

Patent Literature

PTL 1
Japanese Patent Publication No. 4617554
PTL 2
Japanese Patent Publication No. 4757573
PTL 3
Japanese Patent Publication No. 3038707

SUMMARY OF INVENTION

Technical Problem

Further downsizing of small-sized pumps used for sphygmomanometers has been desired; however, the technique disclosed in PTL 1 requires the conversion mechanism, that is, the swing member and the eccentric rotation shaft for converting the rotation of the DC motor that performs typical axial rotation into precession. Consequently, the structure is complicated and the size of the product itself is increased.

In addition, in the field of small-sized pumps such as the small-sized pump disclosed in PTL 1, there is no actuator that can directly cause precession as the driving source. Under such circumstances, for example, it is conceivable to apply the structure disclosed in PTL 2 or PTL 3 in the small-sized pump.

However, the biaxial actuator disclosed in PTL 2 is the VCM type, and therefore high output required for blood pressure measurement cannot be ensured although controllability is high. In addition, in PTL 3, a spring is provided on the back side of the antenna as the movement object, and the region for disposing the spring is required, and as such, it is difficult to achieve reduction in size and thickness.

An object of the present invention is to provide an actuator, an air pump, an aesthetic apparatus and a laser scanning apparatus which have a simple configuration, are easy to assemble, and can provide high output while achieving cost reduction and downsizing by reduction in thickness.

Solution to Problem

An actuator of embodiments of the present invention includes: a movable member including a unipolar magnet magnetized in a unipolar fashion; a fixing member including a plurality of electromagnets each including a core as a magnetic substance and a coil for exciting the core, wherein three or more magnetic poles of the electromagnets are disposed at respective positions orthogonal to a magnetization direction of the unipolar magnet; and an elastic body provided between the movable member and the fixing member, and configured to be elastically deformed when a current is supplied to the coil so as to movably support the movable member in a magnetization direction of the unipolar magnet and in two-degree-of-freedom directions. The elastic body is attached to the movable member such that a movement center of the movable member coincides with an approximate center of a generated magnetic torque of the movable member.

An air pump of embodiments of the present invention includes the above-mentioned actuator. An aesthetic apparatus of embodiments of the present invention includes the above-mentioned actuator. A laser scanning apparatus of embodiments of the present invention includes the above-mentioned actuator.

Advantageous Effects of Invention

The actuator of the embodiments of the present invention has a simple configuration, and is easy to assemble. In addition, the actuator of the embodiments of the present invention can reduce cost with an inexpensive material, and can provide high output while achieving the downsizing.

BRIEF DESCRIPTION OF DRAWINGS

FIG. 6A and FIG. 6B show a cycle of an alternating current supplied from an alternating current supply part to a coil in the actuator;

DESCRIPTION OF EMBODIMENTS

Embodiments of the present invention will be described in detail below with reference to the accompanying drawings.

Embodiment 1

Figure 1:
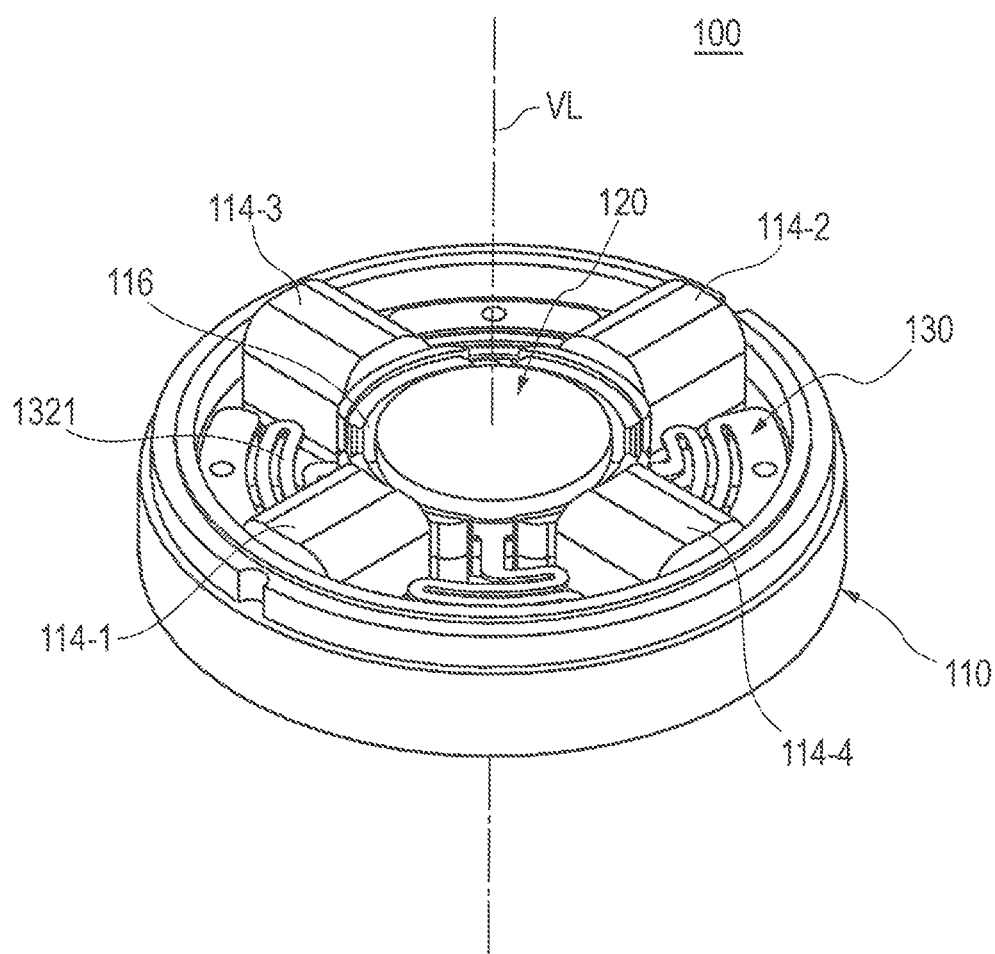
FIG. 1 is a perspective view illustrating an actuator according to Embodiment 1 of the present invention.
Figure 2:
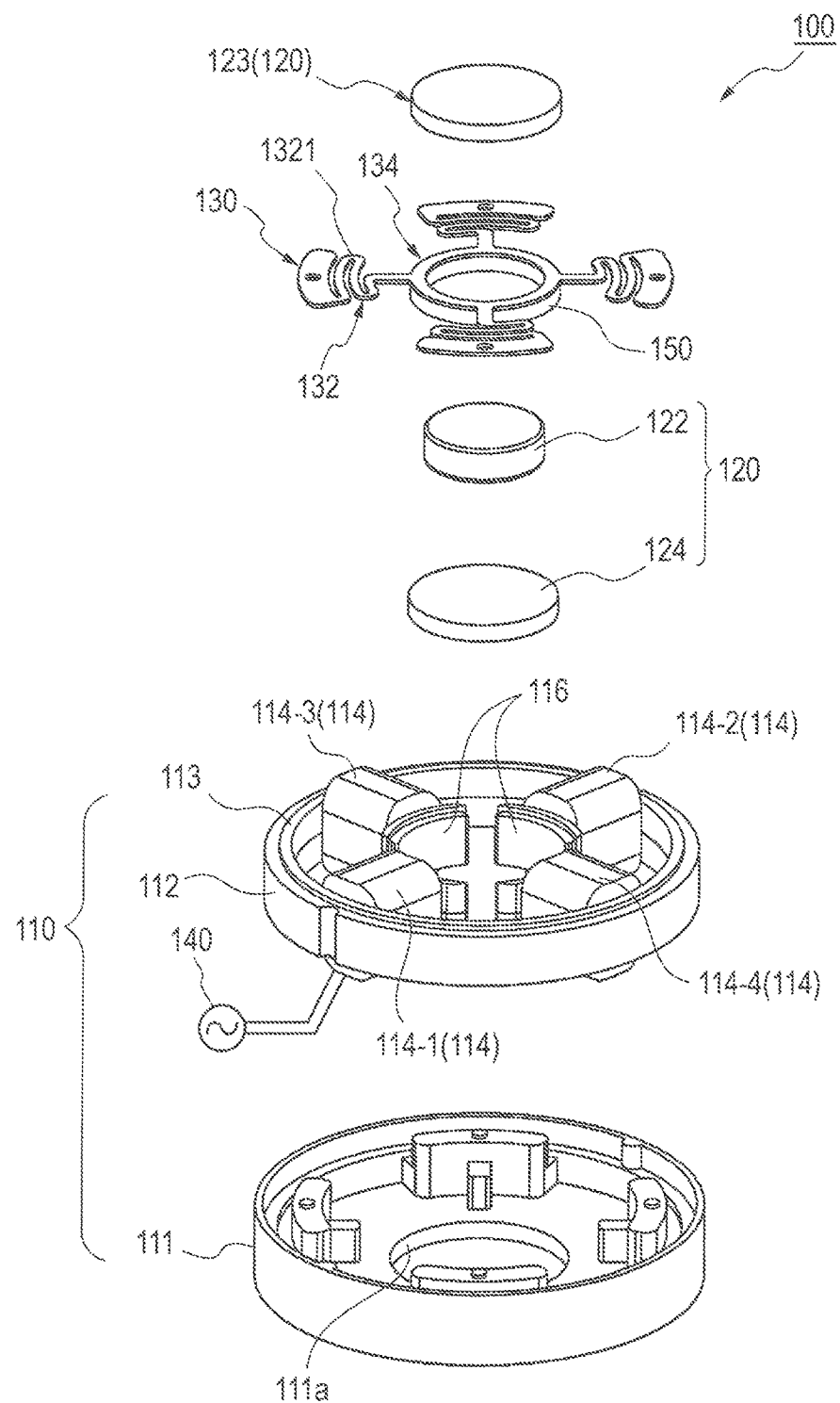
FIG. 2 is an exploded perspective view of a main part of the actuator.

FIG. 1 is a perspective view illustrating an actuator according to Embodiment 1 of the present invention, and FIG. 2 is an exploded perspective view of a main part of the actuator. In addition, FIG. 3 is a schematic sectional view illustrating a configuration of a main part of the actuator.

Actuator 100 illustrated in FIG. 1 and FIG. 2 includes fixing member 110, movable member 120, elastic body (elastic supporting part) 130 that elastically deforms to movably support movable member 120 with respect to fixing member 110, and alternating current supply part 140 (see FIG. 2).

In actuator 100 illustrated in FIG. 1 and FIG. 2, movable member 120 is attached to fixing member 110 such that movable member 120 is movable in multi-degree of freedom directions including the vertical direction (magnetization direction) while the movement in the horizontal direction being restricted. With power supply from alternating current supply part 140, movable member 120 repeats a rotational reciprocation in the forward-and-reverse direction within a predetermined angle range, or to be more specific, a motion of rotating in a twisting direction and returning to the reference position, without using a rotation shaft member, or a member serving as the rotation center. With this configuration, movable member 120 can perform a so-called precession (in two-degree-of-freedom directions).

Figure 3:
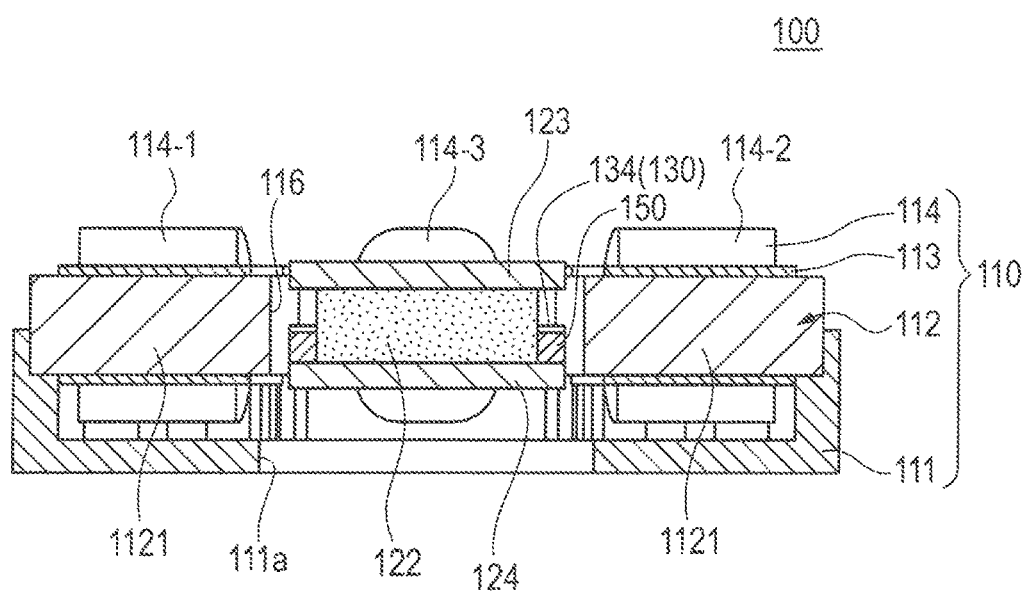
FIG. 3 is a schematic sectional view illustrating a configuration of a main part of the actuator.

As illustrated in FIG. 2 and FIG. 3, fixing member 110 includes fixation base part 111, core part 112, core cover 113, and coil part 114. It is to be noted that core part 112, core cover 113 and coil part 114 serve as an electromagnet unit including electromagnets corresponding to the number of coil parts 114.

Fixation base part 111 is a base of fixing member 110, and here, has a bottomed cylindrical shape, which is provided with opening part 111a formed at a center portion of the bottom surface part. In fixation base part 111, an electromagnet unit is disposed to surround opening part 111a. Inside opening part 111a, movable member 120 is disposed.

Core part 112 includes a plurality of magnetic pole cores 1121 composed of a magnetic substance which form a magnetic pole. Each of magnetic pole cores 1121 is formed in a rod shape, and includes magnetic pole surface 116 at one end thereof. Magnetic pole surface 116 faces unipolar magnet 122 of movable member 120, in a direction that intersects with the magnetization direction of unipolar magnet 122 (here, in a direction orthogonal to the magnetization direction of unipolar magnet 122).

Each magnetic pole core 1121 is covered with core cover 113 having insulation property. Coil part 114 is wound around the outer periphery of magnetic pole core 1121 through core cover 113 having insulation property. Coil part 114 is excited when a current supplied thereto, and thus magnetic pole surface 116 is formed.

In plan view of actuator 100, magnetic pole core 1121 is fixed to fixation base part 111 such that, from the four sides, magnetic pole surfaces 116 face the outer peripheral surface of movable member 120 disposed at a center of fixation base part 111. With this configuration, magnetic pole surfaces 116 are disposed to surround movable member 120 with equal distances therebetween.

Magnetic pole surface 116 is configured in an arc shape facing the outer periphery of movable member 120 (here, a center portion of the outer periphery of unipolar magnet 122) and extending along the outer periphery of movable member 120. Here, magnetic pole surface 116 is composed of an arc-shaped part extending in left and right from one end of magnetic pole core 1121 along the circumferential direction of movable member 120.

Movable member 120 includes unipolar magnet 122, and magnetic substances 123 and 124.

Unipolar magnet 122 has a disk-like shape (for example, coin shape), and the surfaces in the vertical direction of unipolar magnet 122 serve as magnetization surfaces. Here, with respect to fixing member 110, the top surface side of unipolar magnet 122, that is, the surface side, is magnetized to N pole, and the bottom surface side, that is, the rear surface side is magnetized to S pole. Disk-like magnetic substances 123 and 124 are bonded on the respective magnetic pole surfaces of unipolar magnet 122.

Desirably, unipolar magnet 122 is a neodymium-based magnet such as a neodymium magnet and a neodymium bonding magnet or a ferrite-based magnet such as a ferrite magnet and a ferrite bonding magnet, for example. When a neodymium magnet, which is considered to be a strongest permanent magnet, is applied as unipolar magnet 122, the energy conversion efficiency can be increased and downsizing of actuator 100 itself and high output of actuator 100 can be achieved even with a relatively small dimension in comparison with the case where other materials are used, since the magnetic force per volume of the neodymium magnet is strong. In addition, when a ferrite magnet is applied as unipolar magnet 122, the magnetic circuit can be obtained at low cost in comparison with the case where the neodymium magnet is used. Additionally, since a ferrite magnet has a high thermal demagnetization temperature (approximately 200[° C.] while the thermal demagnetization temperature of a neodymium magnet is approximately 130[° C.]), when unipolar magnet 122 is composed of a ferrite magnet, actuator 100 itself can be used in an in-vehicle product.

Movable member 120 is disposed such that the opening part of fixation base part 111 of fixing member 110 is located in the magnetization direction of unipolar magnet 122. In plan view, movable member 120 is supported by elastic body 130 in the state where the center of movable member 120, that is, virtual center line VL, coincides with the center of fixing member 110.

Coil part 114 is wound around the outer periphery of core part 112 extending in a direction that intersects with the magnetization direction of the unipolar magnet, here, in a direction orthogonal to the magnetization direction of the unipolar magnet. Together with core part 112 having magnetic pole surface 116, coil part 114 serves an electromagnet, and is used for the driving of actuator 100. Desirably, the axis of coil part 114 coincides with the axis of magnetic pole core 1121 around which coil part 114 is wound. The coil winding of coil part 114 is connected with a substrate not illustrated (a substrate having a switch and the like), and is connected with an external terminal through the substrate. Coil part 114 is supplied with an alternating current power (AC voltage) from alternating current supply part 140 through the external terminal.

The polarity of coil part 114 corresponds to the polarity of magnetic pole surface 116 of magnetic pole core 1121 around which coil part 114 is wound. The polarity of the magnetic pole surface is appropriately changed by the direction of the supply current. To be more specific, the polarity of the magnetic pole surface is appropriately changed by changing the direction of an alternating current, which is supplied from alternating current supply part 140 to coil part 114, having a frequency substantially equal to the resonance frequency of movable member 120. When a desired coil part 114 is appropriately excited in the above-mentioned manner and this operation is repeated, a torque (magnetism generation torque) for moving movable member 120 is generated, and movable member 120 is moved. Here, oppositely disposed coil parts 114 (specifically, magnetic pole surfaces 116 corresponding to coil parts 114) are excited to different polarities (N pole and S pole), and a torque (magnetism generation torque) in a twisting direction of magnetization magnet 122 is generated through elastic body 130 (see FIG. 4). Another pair of coil parts 114 different from the firstly excited pair of coil parts 114 are excited with respect to movable member 120 displaced in the twisting direction, and this operation is sequentially repeated.

It is to be noted that the number of the magnetic poles of the electromagnet unit is not limited as long as three or more magnetic poles are provided. In the present embodiment, coil parts 114 are excited such that the magnetic poles are alternately different from each other, and, with the torque thus generated, precession of movable member 120 can be achieved. It is to be noted that four or more even-numbered magnetic poles are easier to control than odd-numbered magnetic poles. That is, precession can be readily generated by exciting opposite coil parts 114 to different magnetic poles and by exciting the coil parts adjacent to the firstly excited pair of coil parts 114 at a timing when movable member 120 is moved in a twisting direction, and, by alternately repeating the above-mentioned operations.

At a position between fixing member 110 and movable member 120, a fixed end of elastic body 130 is fixed to fixing member 110, and an idle end of fixing member 110 is fixed to movable member 120. Elastic body 130 is attached to movable member 120 such that the movement center of movable member 120 coincides with the approximate center of the generated magnetic torque of movable member 120.

For example, elastic body 130 is composed of a non-magnetic material such as stainless-steel and phosphor bronze. With this configuration, unnecessary leakage magnetic flux in actuator 100 can be reduced, and the assemblability of actuator 100 itself can be improved.

Here, elastic body 130 is composed of a leaf spring, and with this configuration, the cost of actuator 100 itself can be reduced. In addition, a resin spring may also be used as elastic body 130.

Elastic body 130 includes plate-shaped elastic arm part 132 having a zigzag part whose one end is the fixed end, and ring part 134 connected with the other end of plate-shaped elastic arm part 132 and externally fitted on the periphery of movable member 120.

With zigzag part 1321, plate-shaped elastic arm part 132 has a shape in which the length from the fixed end fixed to fixation base part 111 to the idle end fixed to movable member 120 is greater than that of a straight line shape and a sufficient length for elastic deformation is ensured.

Ring part 134 is integrally fixed to holder 150 that is fitted on the outer periphery of movable member 120. Holder 150 is fixed on magnetic substance 124 in the state where it is disposed at the outer periphery of magnetization magnet 122. With its thickness, holder 150 sets the supporting position with respect to magnetization magnet 122 by elastic body 130, that is, the installation position between fixing member 110 and movable member 120. With this configuration, plate-shaped elastic arm part 132 between fixing member 110 and movable member 120 is fixed to fixing member 110 and movable member 120 so as to be located on the horizontal surface that passes through the approximate center of the generated magnetic torque of movable member 120. Additionally, in plan view, the installation positions of plate-shaped elastic arm parts 132 are symmetric about the approximate center of movable member 120. In the present embodiment, movable member 120 is movably supported through four plate-shaped elastic arm parts 132 disposed on four sides. Elastic body 130 is supported such that movable member 120 is movable with the approximate center of the generated magnetic torque of movable member 120 located on the extensions of the bias direction whose base points are located at positions (fixed ends) connected with movable member 120.

With this configuration, movable member 120 is held by fixing member 110 through elastic body 130 in the state where the approximate center of the generated magnetic torque of movable member 120 coincides with the approximate center between magnetic pole surfaces 116 of core parts 112 in the horizontal direction. Without using a member corresponding to a rotational shaft, a bearing of the shaft or the like, movable member 120 is attached to be movable in the multi-degree of freedom directions including the vertical direction (magnetization direction) with respect to fixing member 110 with the movement in the horizontal direction being restricted.

With elastic body 130, a certain spring constant with respect to the movable direction of unipolar magnet 122 can be obtained, and thus a torque acts on movable member 120. With this configuration, for example, movable member 120 moves in two-degree-of-freedom directions, and here, in a twisting direction (see FIG. 4). By adjusting the spring constant of elastic body 130, the resonance frequency of actuator 100 can be adjusted.

That is, in actuator 100 having the above-mentioned configuration, when an alternating current having a frequency substantially equal to the resonance frequency of movable member 120 is input to coil part 114 and magnetic pole surfaces 116 corresponding to coil parts 114 disposed to face each other are excited to different polarities (N pole and S pole), a magnetic suction force and a resilience are efficiently generated with respect to unipolar magnet 122 of movable member 120. With this configuration, unipolar magnet 122 of movable member 120 performs precession around approximate center G (including the center) of a generated magnetic torque of unipolar magnet 122 as the center so as to turn around virtual center line extending in the vertical direction.

In actuator 100 of the present embodiment, movable member 120 vibrates with respect to fixing member 110 at resonance frequency Fr [Hz] which is calculated with the following expression (1) where the inertia (inertia moment) of movable member 120 is represented by j and the spring constant in the tortional direction is represented by $K_{sp}$.

$$Fr = \frac{1}{2\pi}\sqrt{\frac{K_{sp}}{J}} \qquad \text{[Expression 1]}$$

Fr: resonance frequency [Hz]

In actuator 100 of the present embodiment, alternating current supply part 140 supplies an alternating current having a frequency substantially equal to resonance frequency Fr of movable member 120 to the coil part. With this configuration, movable member 120 can be efficiently driven.

In actuator 100, movable member 120 is supported by a spring-mass structure, that is, movable member 120 is supported by fixing member 110 through elastic body 130. Accordingly, when the coil part is supplied with an alternating current having a frequency equal to resonance frequency Fr of movable member 120, movable member 120 is driven in the resonance state. The motion in a twisting direction generated at this time is transmitted to elastic body 130.

Actuator 100 is driven based on the equation of motion of the following expression (2) and the circuit equation of the following expression (3).

$$J\frac{d^2\theta(t)}{dt^2} = K_t i(t) - K_{sp}\theta(t) - D\frac{d\theta(t)}{dt} - T_{Load} \qquad \text{[Expression 2]}$$

J: inertia moment [Kgm$^2$]
θ(t): angle [rad]
$K_t$: torque constant [Nm/A]
i(t): current [A]

$$e(t) = Ri(t) + L\frac{di(t)}{dt} + K_e\frac{d\theta(t)}{dt} \qquad \text{[Expression 3]}$$

e (t): voltage [V]
R: resistance [Ω]
L: inductance [H]
$K_e$: counter electromotive force multiplier [V/(rad/s)]

That is, inertia moment J [Kgm$^2$], rotation angle θ (t)[rad], torque constant $K_t$ [Nm/A], current i (t) [A], spring constant $K_{sp}$ [Nm/rad], attenuation coefficient D [Nm/(rad/s)], load torque $T_{Load}$ [Nm] and the like in actuator 100 may be appropriately changed as long as Expression (2) is satisfied. In addition, voltage e (t) [V], resistance R[Ω], inductance L [H], and counter electromotive force multiplier $K_e$ [V/(rad/s)] may be appropriately changed as long as Expression (3) is satisfied.

An operation of actuator 100 having the above-mentioned configuration will be described. An alternating current having a frequency substantially equal to the resonance frequency of movable member 120 is supplied from alternating current supply part 140 to each of a pair of opposite coil parts 114, to alternately excite the coils to different polarities (N pole and S pole). With this configuration, a torque in a twisting direction (magnetism generation torque) with respect to movable member 120 is generated. In the present embodiment, the twisting torque is used to move movable member 120.

Figure 4:
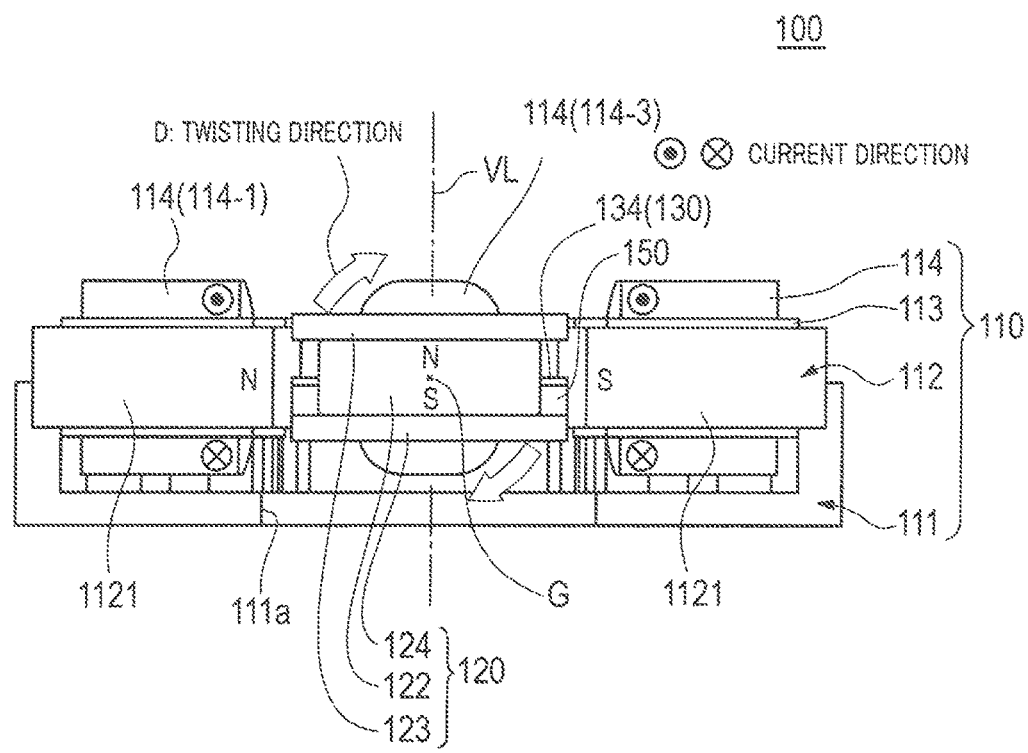
FIG. 4 is a sectional view schematically illustrating a main part for describing an operation of the actuator.
Figure 5A:
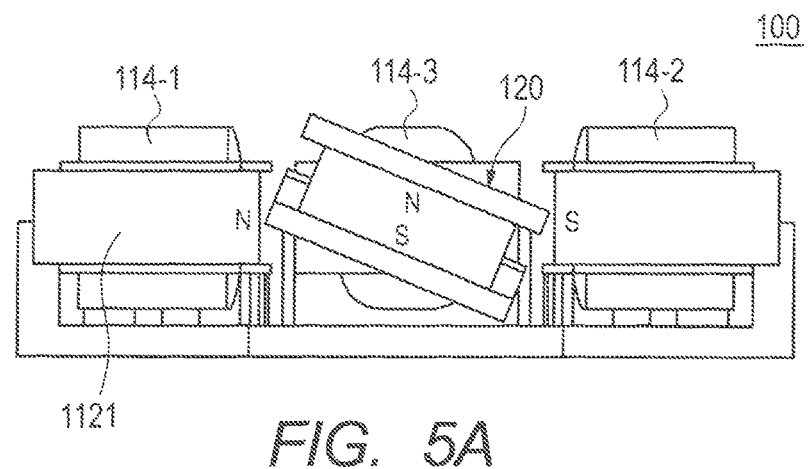
FIG. 5A to FIG. 5C are sectional views schematically illustrating a main part for describing an operation of the actuator.
Figure 5B:
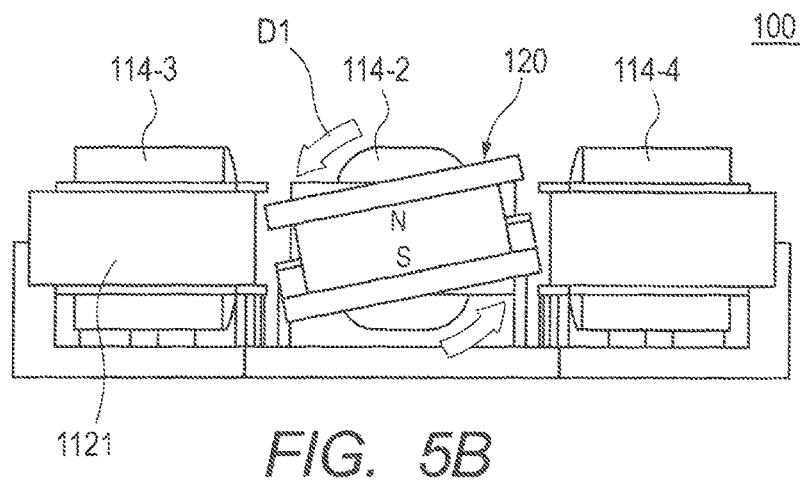
Figure 5C:
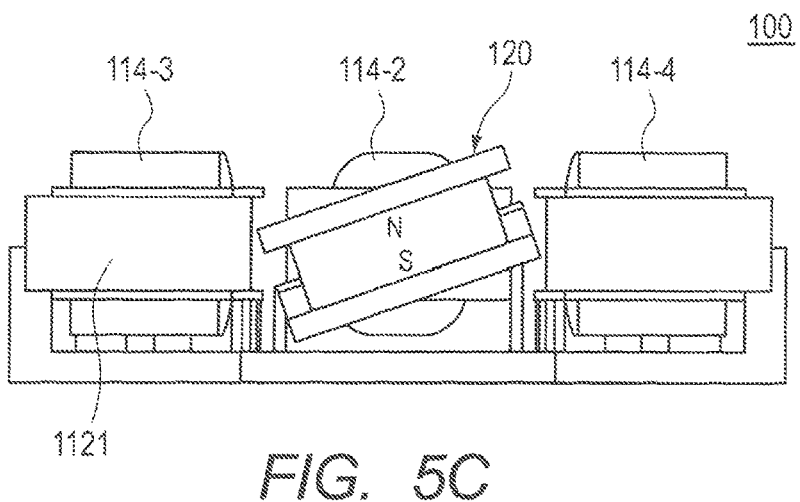

FIG. 4 and FIGS. 5A to 5C are sectional views of a main part for schematically illustrating an operation of actuator 100 according to Embodiment 1 of the present invention. To be more specific, first, the top surface and the bottom surface of unipolar magnet 122 are set to N pole and S pole, respectively, in actuator 100. In this configuration, as illustrated in FIG. 4, an alternating current in the direction indicated in the drawing is supplied to first coil part 114-1 and second coil part 114-2 which have the electromagnets opposite to each other in electromagnets whose magnetic poles are orthogonal to the magnetization direction of unipolar magnet 122 on the outer peripheral surface side of unipolar magnet 122. In response to this power supply, first coil part 114-1 is excited to N pole, and second coil part 114-2 is excited to S pole. With this configuration, according to the Fleming's left hand rule, a thrust is generated, and movable member 120 moves in a twisting direction (arrow D direction) around approximate center G of the generated magnetic torque. This state is illustrated in FIG. 5A. FIG. 5B illustrates third coil part 114-3 adjacent to the excited first coil part 114-1 in the circumferential direction, and fourth coil part 114-4 opposite to third coil part 114-3 in the state of FIG. 5A. In FIG. 5A, with the N pole of first coil part 114-1 and the S pole of second coil part 114-2, movable member 120 is displaced in a twisting direction, and therefore, with respect to third coil part 114-3 and fourth coil part 114-4, movable member 120 is displaced to third coil part 114-3 side against the restoration force of elastic body 130 as illustrated in FIG. 5B.

Next, in the state illustrated in FIG. 5B, third coil part 114-3 adjacent to first coil part 114-1 in circumferential direction is excited to S pole, and fourth coil part 114-4 opposite to third coil part 114-3 is excited to N pole. With this configuration, when being displaced to the horizontal reference position with the restoration force of elastic body 130, movable member 120 moved in the twisting direction is displaced in arrow D1 direction from third coil part 114-3. Next, excitation is performed such that the magnetic pole of first coil part 114-1 is set to S pole, and the magnetic pole of second coil part 114-2 is set to N pole. The coil parts 114 adjacent to each other in the circumferential direction and coil parts 114 opposite to each other are sequentially excited in a unit of the pair of opposite coil parts 114 such that magnetic pole surfaces 116 thereof alternately have different polarities, and thus, movable member 120 is continuously moved. With this configuration, movable member 120 turns around virtual center line VL (see FIG. 1 and FIG. 4) at a predetermined angle to virtual center line VL, that is, movable member 120 performs precession in a circular manner with respect to a base point that passes through virtual center line VL (see FIG. 1 and FIG. 4) and coincides with the approximate center of the generated magnetic torque.

Next, an alternating current supplied to coil part 114 of the present embodiment is briefly described.

FIG. 6A and FIG. 6B illustrate a cycle of an alternating current that is supplied from alternating current supply part 140 to coil part 114 of fixing member 110 in the actuator of the present embodiment.

The alternating current that flows through coil part 114 may be a pulse wave of frequency $f_0$ as illustrated in FIG. 6A, or a sine wave of frequency $f_0$ as illustrated in FIG. 6B.

In the state of FIG. 4, first and second coil parts 114-3 and 114-4 are supplied with a forward current of time point t1 illustrated in FIG. 6A and FIG. 6B, and the opposite magnetic poles are respectively excited to N pole and S pole, thus displacing the movable part in a twisting direction (arrow D direction). The state where movable member 120 is completely displaced in arrow D direction corresponds to time point t2 of FIG. 6A and FIG. 6B, and at time point t2, the direction of the current is switched. The state where movable member 120 moves with the restoration force of elastic body 130 toward the original position and returns to the original position corresponds to time point t3 illustrated in FIG. 6A and FIG. 6B, and the opposite current is supplied to third and fourth coil parts 114-3 and 114-4, for displacement in D1 direction of FIG. 5B. In addition, in the state where movable member 120 is displaced in arrow D1 direction (FIG. 5C), the direction of the current is switched as illustrated in time point t4 of FIG. 6A and FIG. 6B, and movable member 120 is moved to be displaced to the original position from the state of FIG. 5A, and, when movable member 120 returns to the original position, the forward current illustrated in FIG. 6A and FIG. 6B is supplied to first and second coil parts 114-3 and 114-4 at time point t5. The above-mentioned operations correspond to one cycle, and when the above-mentioned operations are repeated, movable member 120 performs precession in a circular manner around virtual center line VL (see FIG. 1 and FIG. 4) of movable member 120 as the base point. It is to be noted that the supply of the alternating current and the switching of the supply destination are performed at a substrate not illustrated that is connected at a position between alternating current supply part 140 and coil part 114.

Actuator 100 of the present embodiment has a simple magnetic circuit configuration, and is easy to assemble. In addition, actuator 100 of the present embodiment can reduce cost with an inexpensive material, and can achieve a high output while achieving the downsizing.

It is to be noted that, in the case where the top surface side and the bottom surface side of unipolar magnet 122 are set to N pole and S pole, respectively, in the actuator 100 having the above-mentioned configuration, a suction force acts on the bottom surface side of unipolar magnet 122 and a resilience acts on the top surface side of unipolar magnet 122 when coil part 114 of fixing member 110 is excited such that all magnetic poles are set to N pole. With this configuration, for example, movable member 120 can be moved upward by excitation of setting all magnetic poles to S pole, and movable member 120 can be moved downward by excitation of setting all magnetic poles to N pole at a timing of returning to the reference position with the restoration force of elastic body 130. That is, by controlling the repeating of the above-mentioned operations with use of the substrate for example, actuator 100 can vibrate movable member 120 in the vertical direction.

In addition, in actuator 100, movable member 120 performs a motion of rotating in a twisting direction and returning to the reference position. When actuator 100 is applied in the conventional small-sized pump disclosed in PTL 1 in place of the DC motor and the eccentric rotation shaft, further downsizing can be achieved in comparison with the conventional small-sized pump. That is, a pump in which actuator 100 of the present embodiment is applied can vertically move the diaphragm in the conventional small-sized pump by only directly connecting the top surface of the movable member and the diaphragm on the bottom surface of the pump chamber without using a conversion mechanism for converting the rotation of the DC motor into precession.

Figure 7:
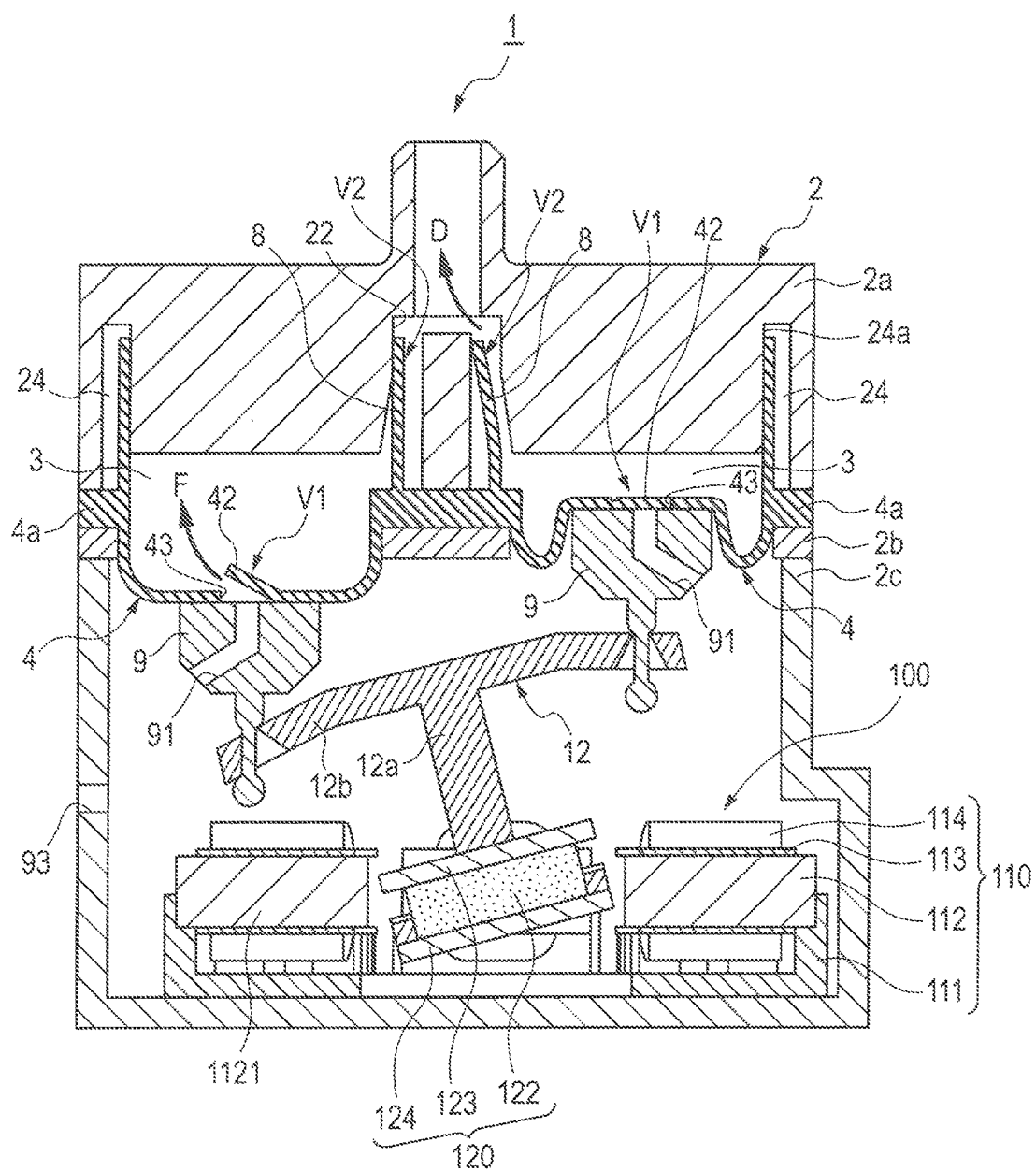
FIG. 7 is a sectional view of a schematic configuration of a main part of an air pump in which the actuator is applied.

An example case is illustrated in FIG. 7.

FIG. 7 illustrates an example air pump in which the actuator of the embodiment of the present invention is applied.

Air pump 1 illustrated in FIG. 7 includes a plurality of (2, in this instance) diaphragms 4, 4 for forming pump chambers 3, 3 in case 2 having a rectangular shape in plan view. Diaphragms 4, 4 are integrally coupled with each other, and attachment protrusions 9, 9 protruding downward are provided at lower center portions of diaphragms 4, 4. It is to be noted that case 2 is configured in a triple-stage of upper case 2a, middle case 2b, and lower case 2c, and diaphragms 4, 4 are held to case 2 with flange parts 4a, 4a of diaphragms 4, 4 tightly attached between upper case 2a and middle case 2b.

Swinging member 12 for vertically moving the bottom surfaces of diaphragms 4, 4 is swingably disposed to attachment protrusions 9, 9. Center portions of the bottoms of diaphragms 4, 4 are partially cut to form suction valves 42, 42. Through holes 43, 43 are provided by the cutting, and through holes 43, 43 can be closed or opened with suction valves 42, 42, and thus suction valve parts V1, V1 are formed. It is to be noted that the way of forming suction valves 42, 42 is not limited to the above-described method, and other method may be adopted.

Each of attachment protrusions 9, 9 includes air introduction hole 91 that is formed to penetrate through the attachment protrusion and is capable of communicating with through hole 43 through suction valve 42 on one end side thereof.

With opening and closing of suction valve 42, attachment protrusions 9, 9 communicate between the inside of the pump chamber and the installation space of the actuator (the inside of lower case 2c) through air introduction hole 91.

On the other hand, upper case 2a is provided with exhaust hole 22 at a center portion thereof. In addition, upper case 2a includes annular groove part 24 that is formed by annularly cutting out the bottom surface of upper case 2a. The upper end portions of diaphragms 4, 4 are inserted to annular groove part 24. Annular groove part 24 is continuous from the both end portions of exhaust hole 22 at a center portion of upper case 2. At inner wall surface 24a of annular groove part 24, exhaust valve parts V2, V2 are formed with pressure contact of exhaust valves 8 composed of upper parts of diaphragms 4, 4.

In addition, swinging member 12 is swingably coupled with a lower end portion of each of diaphragms 4, 4, and swinging member 12 is joined to movable member 120 of actuator 100.

Swinging member 12 includes axial part 12a extending in the magnetization direction from magnetic substance 123 of movable member 120, and swing arm 12b protruding in a direction approximately perpendicular to axial part 12a from an end portion of axial part 12a. At end portions of swing arm 12b, swinging member 12 is swingably coupled with lower end portions of attachment protrusions 9, 9 of lower portions of diaphragms 4. This coupling part may have any configuration as long as the connection is established such that rotation in a desired direction is allowed. It is to be noted that the wall part of lower case 2c on which swinging member 12 is arranged is provided with communication hole 93 that is formed to communicate between the inside and the outside of lower case 2c for introduction of outside air to the inside.

Air pump 1 drives actuator 100 to cause movable member 120 to perform precession. Accordingly, axial part 12a also performs precession, and consequently swing arm 12b swings to vertically move attachment protrusion 9 of the lower end portions of diaphragms 4, 4.

For example, when attachment protrusion 9 of the lower end portion of diaphragm 4 is moved downward by swinging member 12, the inside of diaphragm 4 is set to negative pressure, and thus exhaust valve 8 makes close contact with inner wall surface 24a of annular concave groove 24, that is, exhaust valve part V2 is closed, and in addition, suction valve 42 releases the closed state of through hole 43, that is, suction valve part V1 is brought into an opened state, thus performing suction from air introduction hole 91 to the inside of diaphragm 4, that is, to the inside of pump chamber 3 as indicated with arrow F.

Next, when the lower end portion of diaphragm 4 is moved upward, the inside of diaphragm 4 is set to high pressure, and thus suction valve 42 closes through hole 43 to bring suction valve part V1 into a closed state, and, the diameter of exhaust valve 8 is increased from inner wall surface 24a, whereby exhaust valve part V2 performs exhaust as indicated with arrow D. The air discharged from the inside of exhaust valve 8 passes through annular concave groove 24 and is discharged out of case 2 from exhaust hole 22. It is to be noted that along with the upward movement of diaphragm 4, the inside of lower case 2c is set to negative pressure. Consequently, air is sucked into lower case 2c, that is, case 2 through communication hole 93.

As described, in air pump 1, suction valve part V1 is arranged at a center portion of the bottom of each of diaphragms 4, 4 forming pump chamber 3, and further, exhaust valve part V2 for the performing exhaust of the inside of diaphragm 4 is arranged at a center portion of the upper plate of upper case 2a of case 2 forming the top surface of pump chamber 3. In addition, swinging member 12 that drives diaphragm 4 for sending air out of exhaust valve part V2 is directly joined to movable member 120 of actuator 100. With this configuration, air pump 1 does not require a conversion mechanism for converting the rotation of the DC motor into precession, and the height of air pump 1 is reduced (height reduction), whereby further downsizing is achieved in comparison with the conventional pump.

With the above-mentioned configuration, actuator 100 can be utilized as a driving source for achieving precession similar to the above-mentioned precession, and may be applied to other devices than air pump 1. In addition, while actuator 100 can be applied as a driving source for precession of an air pump and the like, actuator 100 may be used for mirror driving of a laser radar which requires biaxial rotational movement, or may be used in a laser scanner which requires scan function and the like, for example.

In addition, in the case where actuator 100 is used in an aesthetic apparatus such as a massage device as a facial equipment, it suffices to provide the main body of the apparatus on which actuator 100 is attached with a protrusion which can move in and out with the motion of movable member 120.

In addition, actuator 100 operates with a resonance phenomenon which satisfies the Expressions (2) and (3) and uses a resonance frequency represented by Expression (1). With this configuration, in actuator 100, the power consumed in the steady-state is only the loss of the load torque, the loss of the friction and the like, and thus actuator 100 can be driven with small power consumption, that is, movable member 120 can perform precession with small power consumption.

In addition, according to the present embodiment, direct-precession can be achieved with movable member 120 having magnetization magnet 122, and therefore, when actuator 100 is used as the driving source of air pump 1, a conversion mechanism for converting rotational movement into precession is not required unlike the conventional techniques. Thus, further downsizing of air pump 1 can be achieved. Further, since a conversion mechanism from rotational movement into precession is not required unlike the conventional techniques, the slide movement sound generated at the mechanism of converting rotational movement into precession can be reduced. In addition, since such a conversion mechanism is not provided, an actuator having a structure which can be easily assembled with smaller number of components can be achieved.

In addition, for example, in comparison with the two-degree-of-freedom actuator having a conventional support shaft structure disclosed in PTL 3, the rotational shaft of the movable member for moving the movable member, or the positioning shaft is not required. Consequently, the structure can be simplified, and improvement of the assemblability and cost reduction can be achieved.

It is to be noted that, according to actuator 100, elastic body (spring) 130 is disposed at the outer periphery of movable member 120, and thus the thickness can be reduced unlike an actuator having a configuration in which the movable member is supported by the elastic body (spring) fixed at the center of the movable member.

In addition, magnetic substances 123 and 124 are disposed at the magnetic pole surfaces of unipolar magnet 122. With this configuration, unipolar magnet 122 can be used as a part of an efficient magnetic circuit together with the electromagnet unit, and high output can be obtained even with unipolar magnet 122 having a small outer diameter, and consequently, energy conversion efficiency can be increased.

Elastic body 130 is composed of a leaf spring. With this configuration, elastic body 130 can be produced at low cost, and cost reduction can be achieved. Further, the ease of design of the spring constant is increased, and the actuator can be provided as a highly reliable product.

Since movable member 120 is disposed inside fixing member 110, movable member 120 can be composed of a unipolar magnet having a cylinder shape or a rectangular shape, and the actuator can be obtained at low cost so as to achieve cost reduction.

In addition, since elastic body 130 is composed of a non-magnetic material, the magnetic suction force is not generated at the time of assembling actuator 100, and the assemblability of actuator 100 itself can be improved.

Embodiment 2

Figure 8:
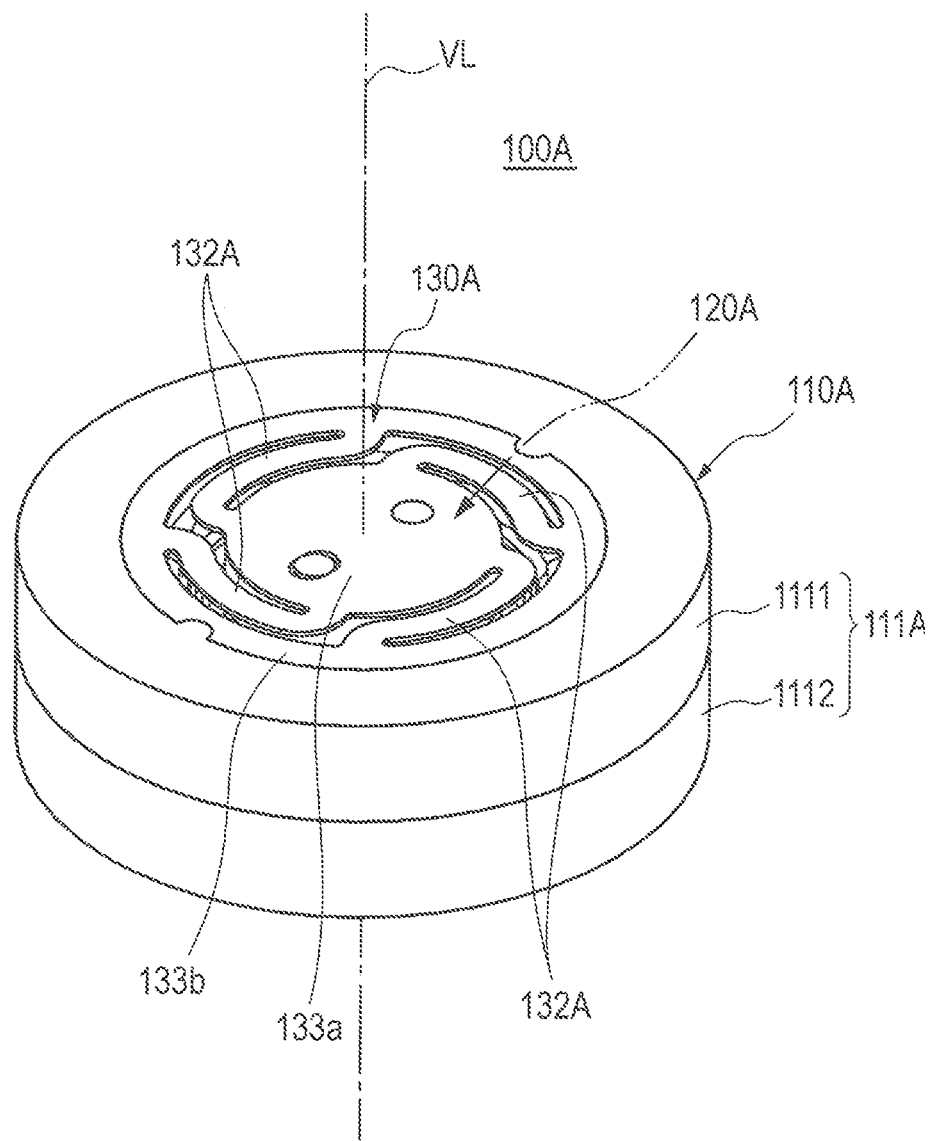
FIG. 8 is a perspective view of an actuator according to Embodiment 2 of the present invention.
Figure 9:
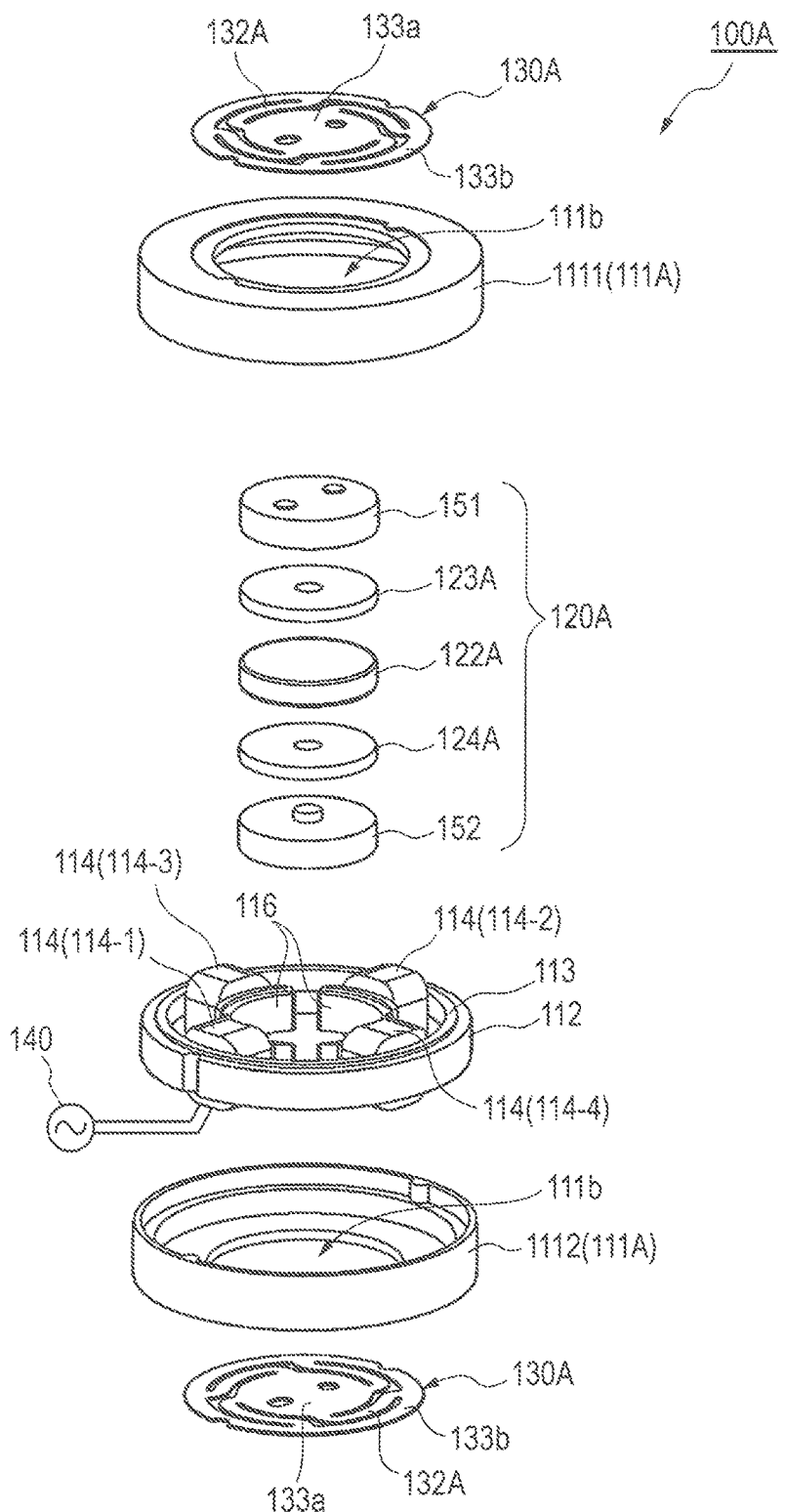
FIG. 9 is an exploded perspective view of a main part of the actuator.
Figure 10:
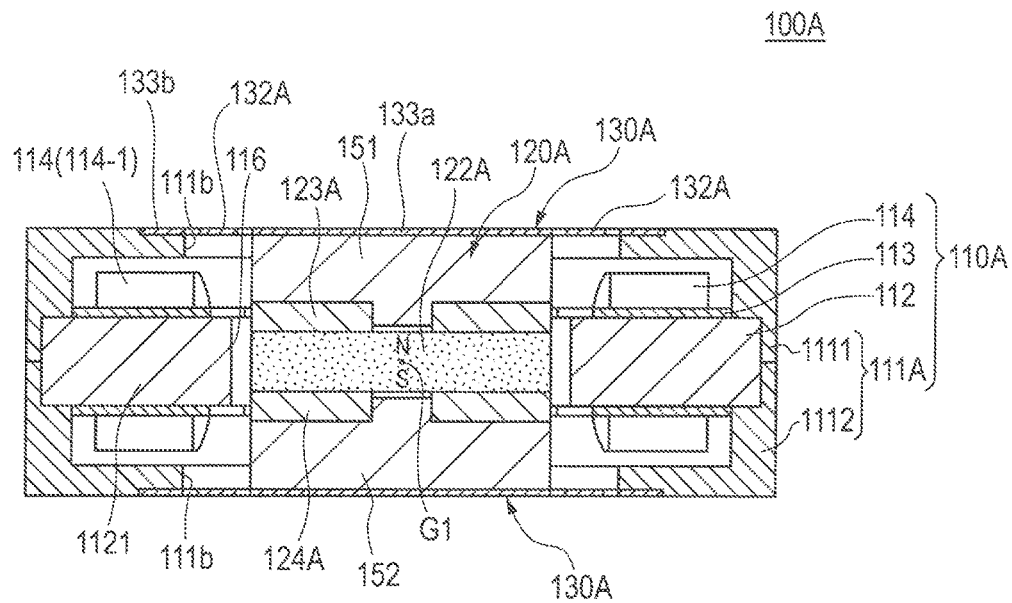
FIG. 10 is a schematic sectional view illustrating a configuration of a main part of the actuator.

FIG. 8 is a perspective view of actuator 100A according to Embodiment 2 of the present invention, FIG. 9 is an exploded perspective view of a main part of the actuator 100A, and FIG. 10 is a schematic sectional view of a configuration of a main part of the actuator 100A.

While movable member 120 is movably supported by one elastic body 130 in Embodiment 1, movable member 120A in Embodiment 2 is supported by two elastic bodies 130A that elastically deform (see FIG. 9 and FIG. 10).

To be more specific, fixation base part 111, elastic body 130 and holder 150 of actuator 100 of Embodiment 1 are replaced by fixation case 111A, two elastic bodies 130A and upper holder 151, and lower holder 152 in actuator 100A of Embodiment 2. That is, actuator 100A has a basic structure similar to that of actuator 100, and is driven by a similar driving principle. Accordingly, the components identical to those of actuator 100 are denoted with the same names and reference numerals, and the description thereof will be omitted.

Actuator 100A illustrated in FIG. 8 to FIG. 10 includes fixing member 110A, movable member 120A, elastic body 130A that movably supports movable member 120A with respect to fixing member 110A, and alternating current supply part 140 (see FIG. 9). Fixing member 110A and movable member 120A have functions similar to those of fixing member 110 and movable member 120 of actuator 100 of Embodiment 1.

Specifically, as with the configuration of movable member 120 of in Embodiment 1, movable member 120A includes a disk-like unipolar magnet 122A. Disk-like magnetic substances 123A and 124A are respectively bonded on the upper and lower magnetic pole surfaces of unipolar magnet 122A in the magnetization direction. Upper holder 151 and lower holder 152 having a predetermined thickness in the magnetization direction (vertical direction) are fixed on magnetic substances 123A and 124A, respectively. Upper holder 151 and lower holder 152 are used for setting the position of elastic body 130A with respect to movable member 120A, that is, magnetization magnet 122A, and here, the thickness of upper holder 151 and lower holder 152 are adjusted such that supporting of elastic body 130A can be achieved. Each of upper holder 151 and lower holder 152 having such a thickness is joined to the idle end of elastic body 130A fixed at the fixed end of fixing member 110, movable member 130A is located at a reference position where it is horizontally provided between fixing member 110A and movable member 120A. With this configuration, two elastic bodies 130A are attached to movable member 120A such that the movement center of movable member 120A coincides with the approximate center (including the center) G1 (see FIG. 10) of a generated magnetic torque of movable member 120A.

Fixing member 110A includes fixation case 111A in which the electromagnet unit of Embodiment 1 is provided.

Fixation case 111A is communicated with outside through opening part 111b opening at the center portion of the top surface and the bottom surface, and in addition, a hollow part in which movable member 120A can be movably disposed is formed inside fixation case 111A. As illustrated in FIG. 9 and FIG. 10, fixation case 111A includes upper case 1111 and lower case 1112 that are separated in the vertical direction.

In upper case 1111 and lower case 1112, an electromagnet unit (core part 112, core cover 113 and coil part 114) is disposed to surround the edge of opening part 111b of the center portion. Each magnetic pole surface 116 of magnetic pole core 1121 of core part 112 is disposed to face the outer peripheral surface of movable member 120A in the hollow part of fixation case 111A.

Elastic body 130A is attached to the opening end portion of opening part 111b at a center of the top surface and bottom surface of upper case 1111 and lower case 1112, so as to close opening part 111b.

Elastic body 130A has a basic configuration similar to that of elastic body 130, and here, is formed with a similar material in a disk-like shape. That is, elastic body 130A includes plate-shaped elastic arm part 132A having a zigzag shape that has a fixed end on the outer periphery side, and an idle end uniformly fixed to internal edge circular plate 133a on the internal circumference side.

The fixed end of plate-shaped elastic arm part 132A having a zigzag shape is joined to outer edge annular part 133b of elastic body 130A, and the idle end thereof is joined to internal edge circular plate 133a. Outer edge annular part 133b is fixed to the opening end portion of opening part 111b of each of upper and lower cases 1111 and 1112, and internal edge circular plate 133a is fixed on the upper and the bottom surfaces of upper holder 151 and lower holder 152.

With this configuration, in elastic body 130A, plate-shaped elastic arm part 132A is attached to horizontally extend along the circumferential direction at a position between the opening end portion of opening part 111b of each of upper and lower cases 1111 and 1112, and the outer edge of each of upper holder 151 and lower holder 152. Plate-shaped elastic arm part 132A of each elastic body 130A is formed along the opening end portion at a position between the opening end portion of opening part 111b of each of upper and lower cases 1111 and 1112, and the outer edge of each of upper holder 151 and lower holder 152. The length of plate-shaped elastic arm part 132A is greater than the straight line distance between the opening end portion of opening part 111b of each of upper and lower cases 1111 and 1112 and the outer edge of each of upper holder 151 and lower holder 152, that is, plate-shaped elastic arm part 132A has a sufficient length for elastic deformation. Elastic body 130A is supported such that movable member 120A is movable with approximate center G1 of the generated magnetic torque of movable member 120A located on the extensions of the bias direction whose base points are located at positions (fixed ends) connected with movable member 120A.

Figure 11:
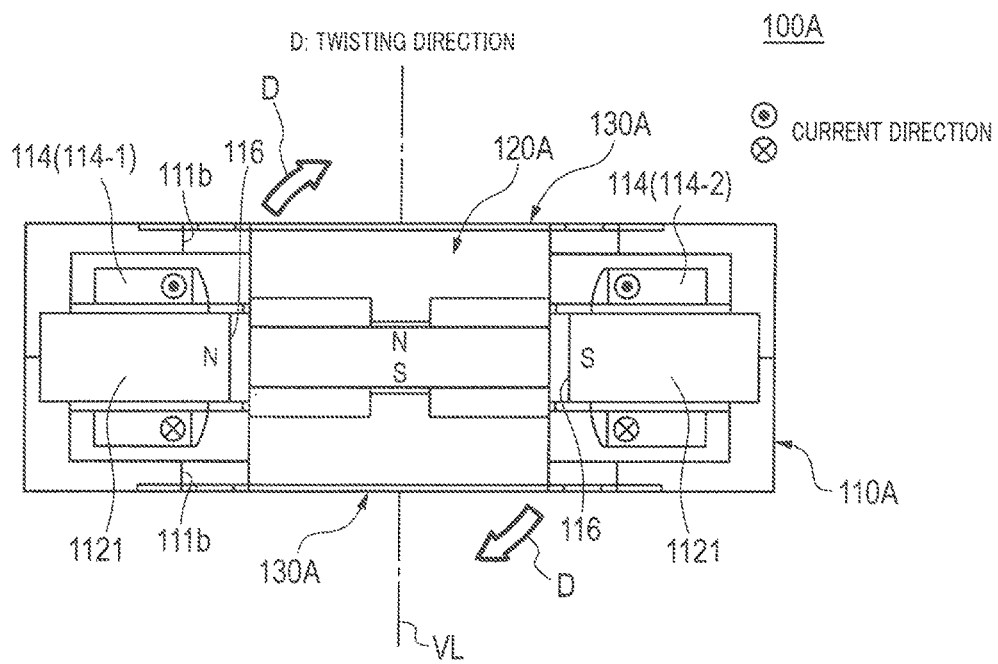
FIG. 11 is a sectional view for describing an operation of the actuator.

In actuator 100A having the above-mentioned configuration, power is supplied from alternating current supply part 140 to coil part 114 of the electromagnet unit of fixing member 110A as with actuator 100. As illustrated in FIG. 11, the alternating current is supplied for excitation such that magnetic pole surface 116 of magnetic pole core 1121 around which first coil part 114-1 is wound is set to N pole, and opposite magnetic pole surface 116 of magnetic pole core 1121 around which second coil part 114-2 is wound is set to S pole.

Consequently, a torque in arrow D direction acts on both of the upper surface side and the bottom surface side, and movable member 120A is displaced in a twisting direction of the D direction. It is to be noted that the coil winding of coil part 114 is connected with a substrate not illustrated (a substrate having a switch and the like). The substrate may control supply of an alternating current power source (AC voltage) supplied to coil part 114 from alternating current supply part 140 connected through the external terminal.

Next, at the time when elastic body 130A returns to the reference position with a restoration force, an alternating current is supplied to third coil part 114-3 adjacent to first coil part 114-1 (see FIG. 9) and fourth coil part 114-4 opposite to third coil part 114-3 (see FIG. 9) to excite the coil parts to magnetic poles different from each other, as with Embodiment 1. To be more specific, third coil part 114-3 and fourth coil part 114-4 opposite to third coil part 114-3 are excited to S pole and N pole, respectively. Then, at the time when elastic body 130A returns to the reference position with the restoration force, third coil part 114-3 adjacent to first coil part 114-1 is excited to N pole, and coil part 114-4 opposite to third coil part 114-3 is excited to S pole. This operation is sequentially and alternately repeated in the circumferential direction, and as a result, movable member 120A performs a motion such as precession in which virtual center line VL of movable member 120A moves in a circular manner (see FIG. 8 and FIG. 11), by a motion principle similar to that of Embodiment 1.

In addition, in Embodiment 2, movable member 120A that performs a motion such as precession is supported by a plurality of elastic bodies 130A such that movable member 120A is movable with respect to fixing member 110A. With this configuration, the stress can be dispersed at the time when an impact is exerted on elastic body 130A. Consequently, problems are less caused, and reliability can be improved. In addition, elastic body 130A provided between fixing member 110A and movable member 120A are disposed on the upper and lower sides of movable member 120A in a sandwiching manner. With this configuration, unlike Embodiment 1, elastic body 130A is not required to be provided inside fixing member 110A, and the degree of freedom of the design of the spring is high in comparison with the configuration of Embodiment 1. The reason for this is that, in the case where elastic body 130 is disposed inside fixing member 110, the installation place of elastic body 130 is determined in advance since the electromagnet unit is also disposed inside fixing member 110, and the spring is required to be designed in the region of the installation place.

In addition, as with actuator 100, actuator 100A has a spring-mass structure. With this configuration, by driving the magnetic circuit with the input frequency to coil part 114 set to a value close to a resonance frequency which can be determined based on the spring constant and the inertia of movable member 120A, the power consumption can be suppressed, and a highly efficient actuator can be provided.

In addition, in actuator 100A, the top surface side and the bottom surface side of unipolar magnet 122A are set to N pole and S pole, respectively, and coil part 114 of fixing member 110A is excited to set all magnetic poles to N pole. Then, a suction force acts on the bottom surface side of unipolar magnet 122A, and a resilience acts on the top surface side. This configuration makes it possible to, for example, move movable member 120A upward by excitation of setting all magnetic poles to S pole, and move movable member 120A downward by excitation of setting all magnetic poles to N pole at a timing of returning to the reference position with restoration force of elastic body 130A. That is, by repeating the above-mentioned operation, actuator 100A can vibrate movable member 120A in the vertical direction as with actuator 100. Such a control of vibration is performed by controlling the supply of power source to coil part 114 with use of a substrate not illustrated.

In addition, actuator 100A may also be used in air pump 1 illustrated in FIG. 7 as with actuator 100. That is, a pump in which actuator 100A of the present embodiment is applied can vertically move the diaphragm in the conventional small-sized pump by only directly connecting the top surface of the movable member and the diaphragm on the bottom surface of the pump chamber without using a conversion mechanism for converting the rotation of the DC motor into precession. With this configuration, further downsizing can be achieved in comparison with the conventional small-sized pump disclosed in PTL 1 that uses a conversion mechanism for converting the rotation of the DC motor into precession.

Actuator 100A may be applied in other devices than air pumps. In addition, while actuator 100A can be applied as a driving source for precession of air pump 1 and the like, actuator 100A may be used for mirror driving of a laser radar which requires biaxial rotational movement, or may be used in a laser scanner which requires scan function and the like, for example. In addition, actuator 100A may be used in a massage device of an aesthetic apparatus and the like as facial equipment for the purpose of downsizing as with actuator 100.

Embodiment 3

Figure 12:
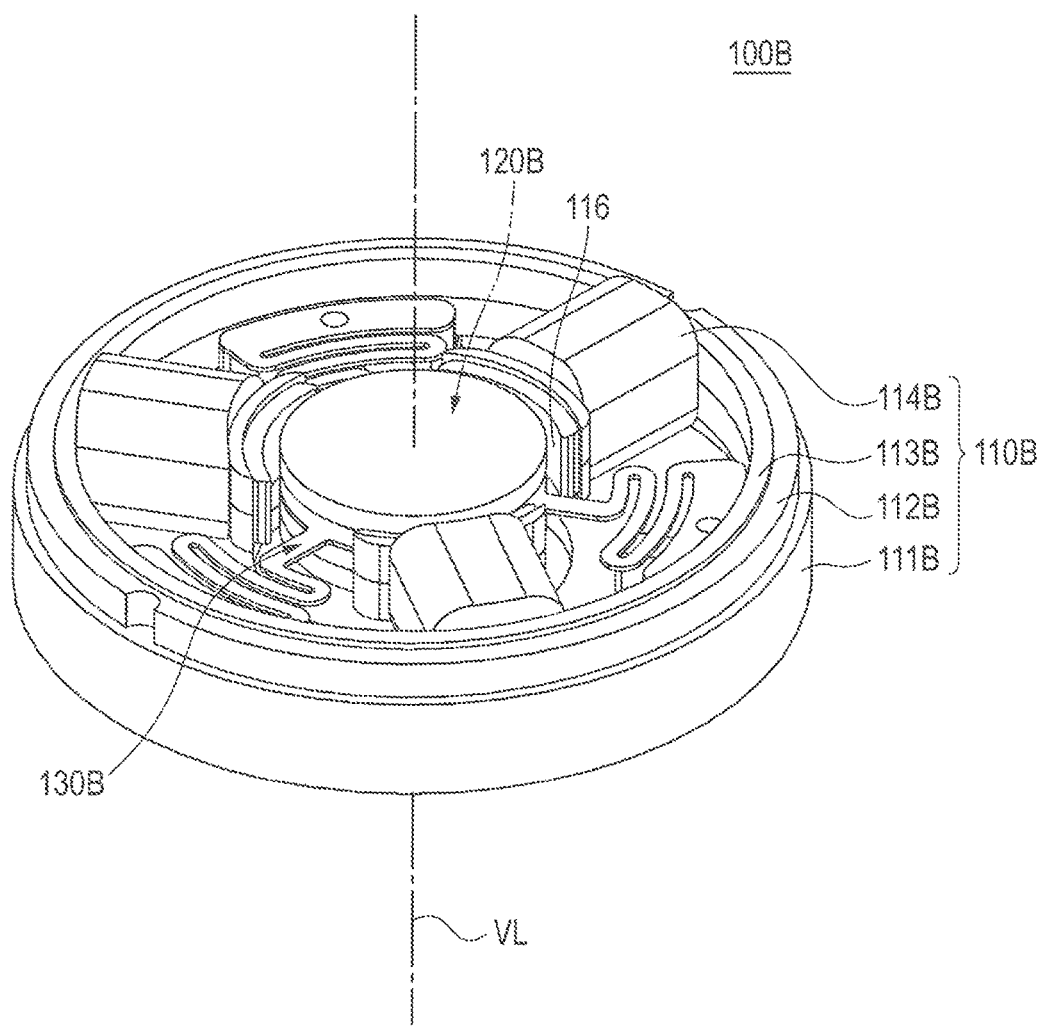
FIG. 12 is a perspective view illustrating an actuator according to Embodiment 3 of the present invention.
Figure 13:
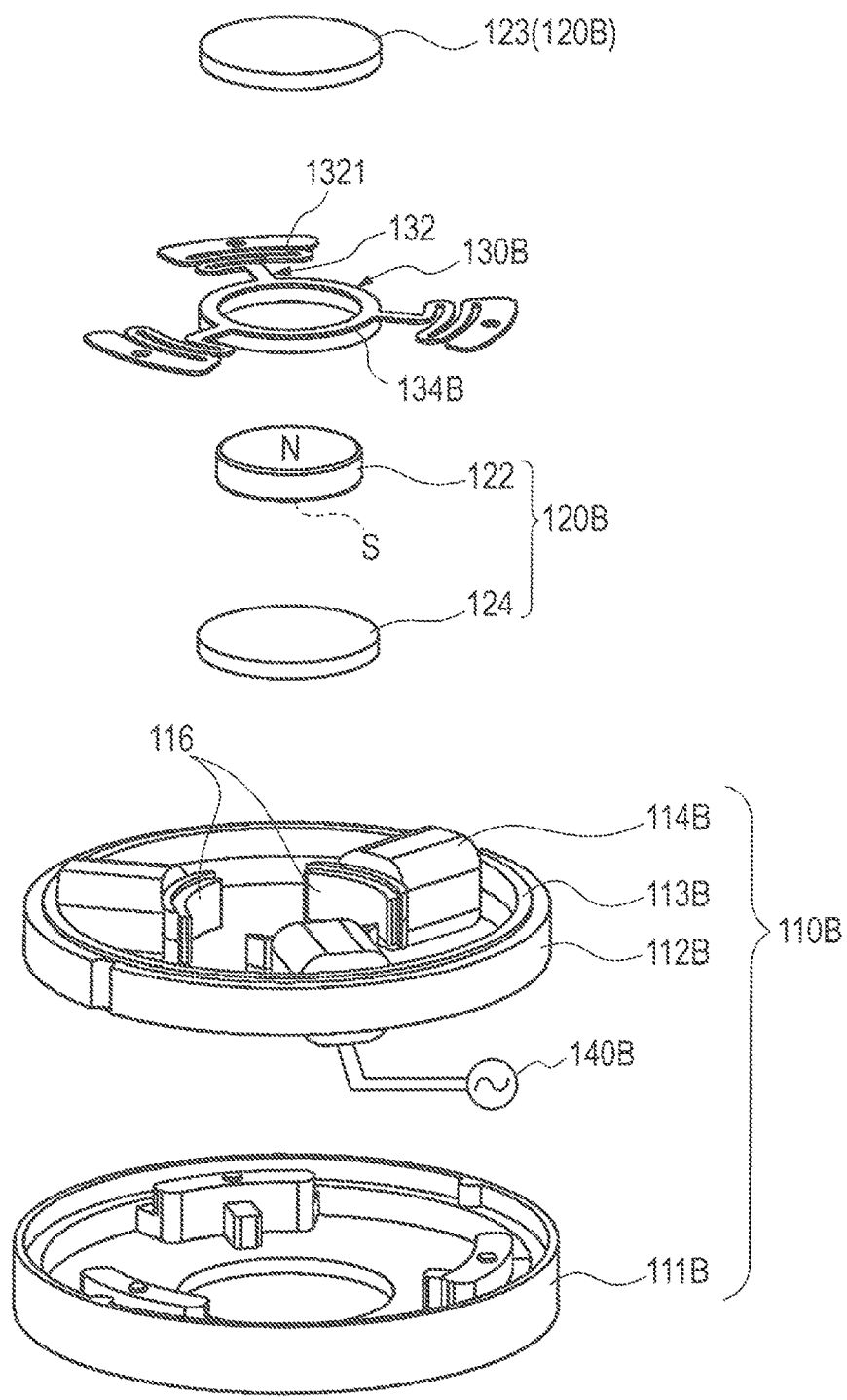
FIG. 13 is an exploded perspective view of a main part of the actuator.

FIG. 12 is a perspective view illustrating actuator 100B according to Embodiment 3 of the present invention, and FIG. 13 is an exploded perspective view of a main part of the actuator 100B. It is to be noted that the schematic sectional view of a main part of actuator 100B is identical to FIG. 3 except for the reference numerals.

Actuator 100B of Embodiment 3 has a basic structure similar to that of actuator 100, and is different from actuator 100 only in the number of the magnetic poles on fixing member 110 side and the number of plate-shaped elastic arm parts 132 of the elastic body. In actuator 100B of Embodiment 3, the number of electromagnet magnetic poles (coil part 114 and magnetic pole core 1121) is set to an odd number, 3, in the configuration of actuator 100 of Embodiment 1.

To be more specific, actuator 100B includes fixing member 110B, movable member 120B, elastic body (elastic supporting part) 130B for movably supporting movable member 120B to fixing member 110B, and alternating current supply part 140B (see FIG. 13).

Movable member 120B has a configuration identical to that of movable member 120, and movable member 120B is attached to fixing member 110B through elastic body 130B such that movable member 120B is movable in the multi-degree of freedom directions including the vertical direction (magnetization direction) while the movement in the horizontal direction being restricted. That is, elastic body 130B is attached to movable member 120B in the state where the movement center of movable member 120B coincides with an approximate center (including the center) of a generated magnetic torque of movable member 120B.

In actuator 100B, movable member 120B moves in a vertical direction or in two-degree-of-freedom directions with respect to fixing member 110B. With power supply from alternating current supply part 140B, movable member 120B repeats a rotational reciprocation in the forward-and-reverse direction within a predetermined angle range, or to be more specific, a motion of rotating in a twisting direction and returning to the reference position, without using a rotation shaft member, or a member serving as the rotation center. With this configuration, movable member 120B can perform so-called precession, that is, a motion of rotating in a circular manner at one end of the axis line passing through the approximate center of a generated magnetic torque of movable member 120B around virtual center line VL at a predetermined angle relative to virtual center line VL.

Fixing member 110B includes fixation base part 111B, core part 112B, core cover 113B, and coil part 114B. It is to be noted that an electromagnet unit is formed with core part 112B, core cover 113B and coil part 114B.

Fixation base part 111B has a bottomed cylindrical shape, and is provided with an opening part at a center portion of the bottom surface part thereof. The electromagnet unit is disposed to surround the opening part at the center of the bottom surface part in fixation base part 111B. In the opening part, movable member 120B is disposed through elastic body 130B.

Core part 112B includes three rod-shaped cores 1121 for forming magnetic poles (see FIG. 3). Magnetic pole cores 1121 is radially disposed with the center opening part at the center on the bottom surface in fixation base part 111B. Magnetic pole surfaces 116 at one ends of magnetic pole cores 1121 are disposed along the outer edge of the opening part at even intervals. Magnetic pole surfaces 116 face unipolar magnet 122 of movable member 120B disposed at a center portion of fixation base part 111B in a direction that intersects with the magnetization direction of unipolar magnet 122 (here, in a direction orthogonal to the magnetization direction of unipolar magnet 122) in such a manner as to surround the outer periphery of unipolar magnet 122. It is to be noted that magnetic pole surface 116 is formed in an arc shape that faces the outer periphery of movable member 120B (here, a center portion of the outer periphery of unipolar magnet 122), and extends along the outer periphery of movable member 120B.

Each of magnetic pole core 1121 of core part 112B (see FIG. 3) is covered with core cover 113B having insulation property. Coil part 114B is wound around the outer periphery of each magnetic pole core 1121 through core cover 113B, and magnetic pole surface 116 is excited when a current is supplied to coil part 114B.

Movable member 120B includes unipolar magnet 122, and magnetic substances 123 and 124, and has a configuration similar to that of movable member 120. Therefore, the description of unipolar magnet 122, and magnetic substances 123 and 124 will be omitted.

With elastic body 130B that elastically deforms, movable member 120B is supported through holder 150 fixed to magnetic substance 124 such that the opening part of fixation base part 111 of fixing member 110B is located in the magnetization direction of unipolar magnet 122. With its thickness, holder 150 sets the supporting position with respect to magnetization magnet 122 by elastic body 130B, that is, the installation position between fixing member 110B and movable member 120B. With this configuration, plate-shaped elastic arm part 132 between fixing member 110B and movable member 120B is fixed to fixing member 110B and movable member 120B so as to be located on the horizontal surface that passes through the approximate center of the generated magnetic torque of movable member 120B. Additionally, in plan view, the installation positions of plate-shaped elastic arm parts 132 are symmetric about the approximate center of movable member 120B. In the present embodiment, movable member 120B is movably supported through three plate-shaped elastic arm parts 132 disposed on three sides. Elastic body 130B is supported such that movable member 120B is movable with the approximate center of the generated magnetic torque of movable member 120B located on the extensions of the bias direction whose base points are located at positions (fixed ends) connected with movable member 120B. In addition, in plan view, at the reference position, the center of movable member 120B (virtual center line VL) coincides with the center of fixing member 110B.

As with coil part 114, coil part 114B is wound around the outer periphery of magnetic pole core 1121 of core part 112B through core cover 113B having insulation property. Together with a magnetic pole core (which has a configuration similar to that of magnetic pole core 1121 illustrated in FIG. 3 and is omitted in the drawing) having magnetic pole surface 116, coil part 114B forms an electromagnet, and is used for driving actuator 100B. Desirably, the axis of coil part 114B coincides with the axis of magnetic pole core (not illustrated) of core part 112 around which coil part 114B is wound. The coil winding of coil part 114B is connected with a substrate not illustrated, and is connected with an external terminal through the substrate. Coil part 114B is supplied with an alternating current power (AC voltage) from alternating current supply part 140B through the external terminal.

The polarity of magnetic pole surface 116 of coil part 114B is appropriately changed by the direction of the supply current. To be more specific, the polarity of magnetic pole surface 116 of coil part 114B is appropriately changed by supplying an alternating current having a frequency substantially equal to the resonance frequency of movable member 120B from alternating current supply part 140B. By appropriately exciting coil part 114B in the above-mentioned manner, and repeating the excitation, movable member 120B is moved.

For example, elastic body 130B is composed of a non-magnetic material such as stainless-steel and phosphor bronze. With this configuration, unnecessary leakage magnetic flux in actuator 100B can be reduced, and the assemblability of actuator 100B itself can be improved. Here, elastic body 130B is composed of a leaf spring, and with this configuration, the cost of actuator 100B itself can be reduced.

Elastic body 130B has a basic configuration similar to that of elastic body 130. That is, elastic body 130B includes plate-shaped elastic arm part 132 having a zigzag part whose one end is the fixed end, and ring part 134B connected with the other end of plate-shaped elastic arm part 132 and externally fitted on the periphery of movable member 120B.

Ring part 134B is integrally fixed to holder 150 that is fitted on the outer periphery of movable member 120B. With this configuration, regarding the installation position of plate-shaped elastic arm part 132 between fixing member 110B and movable member 120B, plate-shaped elastic arm part 132 is disposed at a position where it is paired with magnetic pole surfaces 116 disposed at even intervals and facing the outer periphery of movable member 120B, in a point symmetrical manner about the center of movable member 120B in plan view.

As with Embodiment 1, each plate-shaped elastic arm part 132 is fixed to fixing member 110B and movable member 120B so as to be located on the horizontal surface that passes through the approximate center of the generated magnetic torque of movable member 120B. In the present embodiment, movable member 120B is movably supported through three plate-shaped elastic arm parts 132 disposed on three sides.

With this configuration, movable member 120B is held by fixing member 110B through elastic body 130B in the state where the center of movable member 120B coincides with the center between each magnetic pole surface 116 of core part 112 in the horizontal direction. Movable member 120B is attached to fixing member 110B such that movable member 120B is movable in the multi-degree of freedom directions including the vertical direction (magnetization direction) while the movement in the horizontal direction being restricted without using a member corresponding to a rotational shaft, a bearing of the shaft or the like.

With elastic body 130B, a certain spring constant with respect to the turning direction of unipolar magnet 122 can be obtained, and a torque acts on movable member 120B. With this configuration, movable member 120B is moved in a twisting direction as with movable member 120 (see FIG. 4). That is, with elastic body 130B, the resonance frequency of actuator 100B can be adjusted.

In actuator 100B having the above-mentioned configuration, magnetic pole core 1121, or to be more specific, magnetic pole surface 116 is magnetized with the alternating current waves input to coil part 114B, and a magnetic suction force and a resilience are efficiently generated with respect to unipolar magnet 122 of movable member 120.

Since three magnetic poles are provided, three coil parts 114B are provided with currents whose phases are shifted by 120 degrees. With this configuration, the current with the phase shift is sequentially supplied in the circumferential direction to control movable member 120B to perform precession such that virtual center line VL of movable member 120 moves in a circular manner (see FIG. 1 and FIG. 4) as with the four-pole structure (actuator 100).

It is to be noted that actuator 100B operates with a resonance phenomenon which satisfies the Expressions (2) and (3) and uses a resonance frequency represented by Expression (1) as with actuator 100. With actuator 100B, the number of coil parts 114 can be reduced (from 4 to 3), and man hours can be reduced in comparison with actuator 100. In addition, since the number of the switching devices (e.g., MOSFET) of the driving circuit not illustrated can be reduced, the cost can be further reduced.

In addition, in actuator 100B, the top surface side and the bottom surface side of unipolar magnet 122B are set to N pole and S pole, respectively, and coil part 114B of fixing member 110B is excited to set all magnetic poles to N pole. Then, a suction force acts on the bottom surface side of unipolar magnet 122B, and a resilience acts on the top surface side thereof. This configuration makes it possible to, for example, move movable member 120B upward by excitation of setting all magnetic poles to S pole, and move movable member 120B downward by excitation of setting all magnetic poles to N pole at a timing when elastic body 130B returns to the reference position with the restoration force. That is, by repeating the above-mentioned operation, actuator 100B can vibrate movable member 120B in the vertical direction as with actuator 100.

In addition, as with actuator 100, actuator 100B may also be used in air pump 1 illustrated in FIG. 7. That is, a pump in which actuator 100B of the present embodiment is applied can vertically move the diaphragm in the conventional small-sized pump by only directly connecting the top surface of the movable member and the diaphragm on the bottom surface of the pump chamber without using a conversion mechanism for converting the rotation of the DC motor into precession. With this configuration, in comparison with the conventional small-sized pump disclosed in PTL 1 using a conversion mechanism for converting the rotation of the DC motor into precession, further downsizing can be achieved.

Actuator 100B may be applied in other devices than air pumps. In addition, while actuator 100B can be applied as a driving source for precession of air pump 1 and the like, actuator 100B may be used for mirror driving of a laser radar which requires biaxial rotational movement, or may be used in a laser scanner which requires scan function and the like, for example. In addition, actuator 100B may be used in a massage device of an aesthetic apparatus and the like as facial equipment for the purpose of downsizing as with actuator 100.

Embodiment 4

In Embodiment 4, actuator 100C including electromagnets which form even-numbered magnetic poles drives movable member 120 by changing the polarity of the excited electromagnet as with actuator 100 of Embodiment 1.

Figure 14:
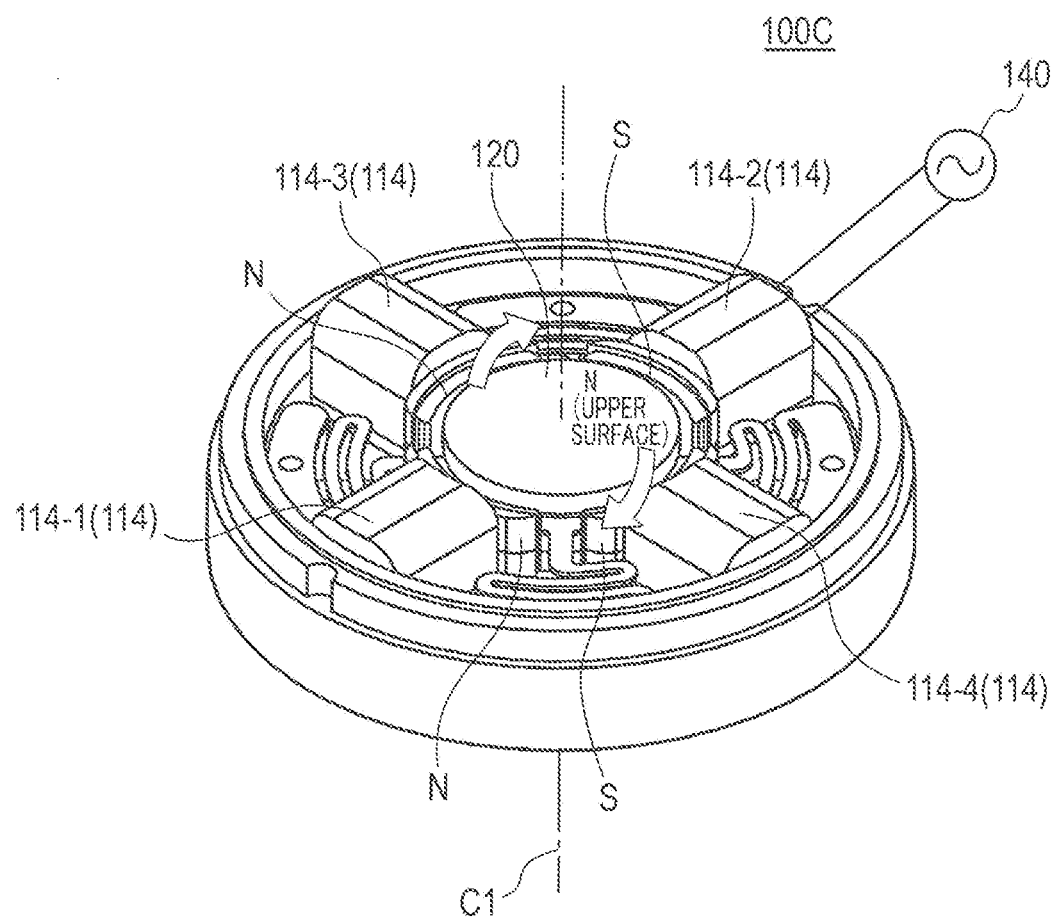
FIG. 14 is a perspective view illustrating an actuator according to Embodiment 4 of the present invention.

Actuator 100C illustrated in FIG. 14 has a configuration similar to that of actuator 100. That is, fixing member 110 includes even-numbered (here, 4) electromagnets disposed at even intervals around unipolar magnet 122. In addition, movable member 120 has a configuration in which magnetic substances 123 and 124 are attached to the both magnetic pole surfaces of unipolar magnet 122 having a magnetization direction set to the vertical direction and surrounded by the electromagnets. The top surface and the bottom surface of unipolar magnet 122 are magnetized to N pole and S pole, respectively.

In actuator 100C having the above-mentioned configuration, the magnetic poles of adjacent two electromagnets of a first group of (electromagnets including first coil part 114-1 and third coil part 114-3) are set to one magnetic pole (for example, N pole) with excitation, and the magnetic poles of electromagnets of a second group (electromagnets including second coil part 114-2 and fourth coil part 114-4) other than the electromagnets of the first group are set to the other magnetic pole (for example, S pole) opposite to that of the electromagnets of the first group with excitation.

Then, movable member 120 is displaced in a direction tilted relative to the movement center. In addition, at the timing when movable member 120 is tilted and returned to the original position (reference position), the direction of the current of the power source supplied to the electromagnets of each group (to be more specific, coil part 114) is reversed. Consequently, at the timing when movable member 120 moves to the original position with the restoration force of elastic body 130, the movable member is tilted in the direction opposite to the preceding orientation with respect to center C1 with electromagnets of the first group and the second group respectively excited to the magnetic pole different from the preceding polarity. By repeating this operation, movable member 120 performs a reciprocation swing motion around center line C with respect to center line C1. With this configuration, actuator 100C can vibrate movable member 120, and can be used as a power generator. In addition, actuator 100C may be used in a massage device of an aesthetic apparatus and the like as facial equipment for the purpose of downsizing as with actuator 100.

It is to be noted that, regarding the polarities of the upper and lower magnetic pole surfaces in the embodiments, the top surface side, that is, the surface side and the bottom surface side, that is, the rear surface side may be magnetized to S pole and N pole, respectively. In this case, in actuators 100, 100A, and 100B, the magnetic circuit of fixing members 110, 110A, and 110B side is changed to achieve motions similar to the motions of movable members 120, 120A, and 120B of the above-described actuators 100, 100A, and 100B. To be more specific, the direction of the current in corresponding coil parts 114 and 114B is changed to the opposite direction.

In addition, actuators 100, 100A, 100B, and 100C of the embodiments are configured as an inner rotor type in which the magnetic poles is located on the outer periphery side of movable member 120. With this configuration, unlike the case of the outer rotor type in which the movable member is disposed outside the fixing part, it is not required to separately provide the mechanism for holding the movable member outside the movable member, and the thickness can be further reduced. Further, actuators 100, 100A, 100B, and 100C can adopt the PM driving scheme, and therefore can increase the output in comparison with the VCM driving type.

The present invention is not limited to the above-described embodiments, and various variations and modifications may be possible without departing from the scope of the present invention.

The embodiment disclosed herein is merely an exemplification and should not be considered as limitative. The scope of the present invention is specified by the following claims, not by the above-mentioned description. It should be understood that various modifications, combinations, sub-combinations and alterations may occur depending on design requirements and other factors in so far as they are within the scope of the appended claims or the equivalents thereof. Although embodiments of the present invention has been described and illustrated in detail, it is clearly understood that the same is by way of illustrated and example only and is not to be taken by way of limitation, the scope of the present invention being interpreted by terms of the appended claims.

This application is entitled to and claims the benefit of Japanese Patent Application No. 2014-091860 dated Apr. 25, 2014, the disclosure of which including the specification, drawings and abstract is incorporated herein by reference in its entirety.

INDUSTRIAL APPLICABILITY

The actuator according to the embodiments of the present invention can be easily assembled with a simple configuration, and can provide an effect of achieving high output while achieving cost reduction, and downsizing by thickness reduction. The actuator according to the embodiments of the present invention is suitable for an actuator which can be applied to a device for causing precession of a movable member.

REFERENCE SIGNS LIST 100, 100A, 100B, 100C Actuator
110, 110A, 110B Fixing member
111, 111B Fixation base part
111A Fixation case
111a, 111b Opening part
112, 112B Core part
113, 113B Core cover
114, 114B Coil part
116 Magnetic pole surface
120, 120A, 120B Movable member
122, 122A Unipolar magnet (magnetization magnet)
123, 123A, 124, 124A Magnetic substance
130, 130A, 130B Elastic body
132, 132A Plate-shaped elastic arm part
134, 134B Ring part
140, 140B Alternating current supply part
150, 151, 152 Holder
1111 Upper case
1112 Lower case
1121 Magnetic pole core
1321 Zigzag part

The invention claimed is:

1. An actuator comprising:
a movable member including a unipolar magnet magnetized in a unipolar fashion;
a fixing member including a plurality of electromagnets each including a core as a magnetic substance and a coil for exciting the core, wherein three or more magnetic poles of the electromagnets are disposed at respective positions orthogonal to a magnetization direction of the unipolar magnet; and
an elastic body provided between the movable member and the fixing member, and configured to be elastically deformed when a current is supplied to the coil so as to movably support the movable member in a magnetization direction of the unipolar magnet and in two-degree-of-freedom directions, wherein:
the elastic body is attached to the movable member such that a movement center of the movable member coincides with an approximate center of a generated magnetic torque of the movable member,
the elastic body comprising:
a ring part externally fitted on a periphery of the movable member; and
a plurality of elastic arm parts extending outwardly from the ring part and connected with the fixing member, and
each of the plurality of elastic arm parts is disposed between adjacent electromagnets of the plurality of electromagnets on a horizontal plane that passes through the approximate center of the generated magnetic torque.

2. The actuator according to claim 1, wherein the electromagnets move the unipolar magnet in the two-degree-of-freedom directions with sequential excitation of the magnetic poles such that the movable member performs precession.

3. The actuator according to claim 1, wherein the movable member includes magnetic substances provided on respective magnetic pole surfaces of the unipolar magnet.

4. The actuator according to claim 1, wherein the elastic body is a leaf spring.

5. The actuator according to claim 1, wherein the unipolar magnet is movably disposed at a position where the unipolar magnet is surrounded by the electromagnets.

6. The actuator according to claim 1, wherein the unipolar magnet is a neodymium magnet.

7. The actuator according to claim 1, wherein the unipolar magnet is a ferrite magnet.

8. The actuator according to claim 1, wherein the elastic body is composed of a non-magnetic material.

9. The actuator according to claim 1, wherein the movable member is supported by a plurality of the elastic bodies.

10. The actuator according to claim 1, wherein an input frequency of power supplied to the electromagnets is substantially equal to a rotation resonance frequency of the movable member.

11. An air pump comprising the actuator according to claim 1.

12. An aesthetic apparatus comprising the actuator according to claim 1.

13. A laser scanning apparatus comprising the actuator according to claim 1.

14. The actuator according to claim 1, wherein:
- the fixing member includes N (N is an even number) electromagnets disposed around the unipolar magnet at even intervals; and
- the N electromagnets allow the movable member to reciprocate in a direction tilted with respect to the movement center when magnetic poles of N/2 electromagnets of a first group adjacent to each other are set to one magnetic pole with excitation, and magnetic poles of remaining N/2 electromagnets of a second group which are opposite to the N/2 electromagnets of the first group are set to the other magnetic pole opposite to that of the electromagnets of the first group with excitation.

15. The actuator according to claim 1, wherein each of the plurality of elastic arm parts comprises a zigzag part extending in a zigzag manner between the adjacent electromagnets on the horizontal plane.

\* \* \* \* \*